(12) United States Patent
Cork et al.

(10) Patent No.: US 7,217,356 B2
(45) Date of Patent: *May 15, 2007

(54) MEDICAL SYSTEM, METHOD AND APPARATUS EMPLOYING MEMS

(75) Inventors: William H. Cork, Lake Bluff, IL (US); James J. Ulmes, Lake Zurich, IL (US); Richard L. West, Lake Villa, IL (US); Ying-Cheng Lo, Green Oaks, IL (US); Mark C. Weber, Algonquin, IL (US); Kyungyoon Min, Gurnee, IL (US)

(73) Assignee: Fenwal, Inc., Round Lake, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/198,804

(22) Filed: Aug. 5, 2005

(65) Prior Publication Data

US 2005/0269250 A1    Dec. 8, 2005

Related U.S. Application Data

(63) Continuation of application No. 10/031,112, filed as application No. PCT/US01/21188 on Jul. 3, 2001, now Pat. No. 6,994,781.

(60) Provisional application No. 60/216,640, filed on Jul. 7, 2000.

(51) Int. Cl.
*B01D 61/32* (2006.01)

(52) U.S. Cl. .............. 210/96.1; 210/143; 436/52; 436/63; 604/6.01; 604/6.07; 604/65

(58) Field of Classification Search ............. 210/96.1, 210/143; 436/52, 63; 604/6.01, 6.07, 65
See application file for complete search history.

(56) References Cited

U.S. PATENT DOCUMENTS 4,006,743 A * 2/1977 Kowarski .................. 600/309

(Continued)

FOREIGN PATENT DOCUMENTS

DE         26 36 290         2/1978

(Continued)

OTHER PUBLICATIONS

Jain, "Biochips and Microarrays—Technology and Commercial Potential," Informa Publishing Group Ltd., 2000.

(Continued)

*Primary Examiner*—Terry K. Cecil
(74) *Attorney, Agent, or Firm*—Cook, Alex, McFarron, Manzo, Cummings & Mehler, Ltd.

(57) ABSTRACT

A biological suspension processing system is disclosed that may include a suspension treatment device for treating one or more components of a biological suspension, a first fluid flow path for introducing a suspension into the treatment device and a second fluid flow path for withdrawing a constituent of the suspension from the device. At least one microelectromechanical (MEM) sensor communicates with one of the fluid flow paths for sensing a selected characteristic of the fluid therewith. The MEM sensor may be located elsewhere, such as on a container or bag and communicate with the interior for sensing a characteristic of the fluid contained therein. A wide variety of characteristics may be sensed, such as flow rate, pH, cell type, cell antigenicity, DNA, viral or bacterial presence, cholesterol, hematocrit, cell concentration, cell count, partial pressure, pathogen presence, or viscosity.

20 Claims, 15 Drawing Sheets

U.S. PATENT DOCUMENTS

| | | | |
|---|---|---|---|
| 4,114,802 A | 9/1978 | Brown | |
| 4,303,193 A | 12/1981 | Latham, Jr. | |
| 4,370,983 A | 2/1983 | Lichtenstein | |
| 4,379,452 A | 4/1983 | DeVries | |
| 4,436,620 A | 3/1984 | Bellotti et al. | |
| 4,479,760 A | 10/1984 | Bilstad et al. | |
| 4,526,515 A | 7/1985 | DeVries | |
| 4,637,813 A | 1/1987 | DeVries | |
| 4,894,343 A | 1/1990 | Tanaka et al. | |
| 4,895,805 A | 1/1990 | Sato et al. | |
| 4,908,112 A | 3/1990 | Pace | |
| 4,935,345 A | 6/1990 | Guilbeau et al. | |
| 4,960,177 A | 10/1990 | Holm-Kennedy et al. | |
| 5,078,671 A | 1/1992 | Dennehey et al. | |
| 5,120,303 A | 6/1992 | Hombrouckx | |
| 5,178,603 A | 1/1993 | Prince | |
| 5,189,777 A | 3/1993 | Guckel et al. | |
| 5,252,294 A | 10/1993 | Kroy et al. | |
| 5,267,956 A | 12/1993 | Beuchat | |
| 5,273,517 A | 12/1993 | Barone et al. | |
| 5,296,114 A | 3/1994 | Manz | |
| 5,308,757 A | 5/1994 | Kawamura et al. | |
| 5,316,667 A | 5/1994 | Brown et al. | |
| 5,357,807 A | 10/1994 | Guckel et al. | |
| 5,437,598 A * | 8/1995 | Antwiler | 494/1 |
| 5,445,506 A | 8/1995 | Afflerbaugh et al. | |
| 5,496,265 A | 3/1996 | Langley et al. | |
| 5,506,175 A | 4/1996 | Zhang et al. | |
| 5,507,525 A * | 4/1996 | Leuenberger | 283/67 |
| 5,585,069 A | 12/1996 | Zanzucchi et al. | |
| 5,619,177 A | 4/1997 | Johnson et al. | |
| 5,635,358 A | 6/1997 | Wilding et al. | |
| 5,637,469 A | 6/1997 | Wilding et al. | |
| 5,639,423 A | 6/1997 | Northrup et al. | |
| 5,644,395 A | 7/1997 | Folta | |
| 5,646,039 A | 7/1997 | Northrup et al. | |
| 5,656,785 A | 8/1997 | Trainor et al. | |
| 5,661,235 A | 8/1997 | Bonin | |
| 5,674,742 A | 10/1997 | Northrup et al. | |
| 5,681,484 A | 10/1997 | Zanzucchi et al. | |
| 5,710,466 A | 1/1998 | Allen et al. | |
| 5,726,751 A | 3/1998 | Altendorf et al. | |
| 5,744,366 A | 4/1998 | Kricka et al. | |
| 5,744,902 A | 4/1998 | Vig | |
| 5,755,942 A | 5/1998 | Zanucchi et al. | |
| 5,788,468 A | 8/1998 | Dewa et al. | |
| 5,801,057 A | 9/1998 | Smart et al. | |
| 5,827,481 A | 10/1998 | Bente et al. | |
| 5,836,750 A | 11/1998 | Cabuz | |
| 5,846,396 A | 12/1998 | Zanucchi et al. | |
| 5,856,174 A | 1/1999 | Lipshutz et al. | |
| 5,858,804 A | 1/1999 | Zanzucchi et al. | |
| 5,862,003 A | 1/1999 | Saif et al. | |
| 5,863,708 A | 1/1999 | Zanucchi et al. | |
| 5,866,345 A | 2/1999 | Wilding et al. | |
| 5,876,187 A | 3/1999 | Afromowitz et al. | |
| 5,877,580 A | 3/1999 | Swierkowski | |
| 5,887,009 A | 3/1999 | Mandella et al. | |
| 5,890,745 A | 4/1999 | Kovacs | |
| 5,905,007 A | 5/1999 | Ho et al. | |
| 5,909,069 A | 6/1999 | Allen et al. | |
| 5,909,280 A | 6/1999 | Zavracky | |
| 5,910,252 A | 6/1999 | Truitt et al. | |
| 5,912,181 A | 6/1999 | Petcavich | |
| 5,916,776 A | 6/1999 | Kumar | |
| 5,919,364 A | 7/1999 | Lebouitz et al. | |
| 5,921,678 A | 7/1999 | Desai et al. | |
| 5,922,591 A | 7/1999 | Anderson et al. | |
| 5,927,547 A | 7/1999 | Papen et al. | |
| 5,928,880 A | 7/1999 | Wilding et al. | |
| 5,932,100 A * | 8/1999 | Yager et al. | 210/634 |
| 5,932,794 A | 8/1999 | Fabinski et al. | |
| 5,955,029 A | 9/1999 | Wilding et al. | |
| 5,958,344 A | 9/1999 | Levine et al. | |
| 5,961,767 A | 10/1999 | Aksyuk et al. | |
| 5,964,242 A | 10/1999 | Slocum | |
| 5,971,355 A | 10/1999 | Biegelsen et al. | |
| 5,975,485 A | 11/1999 | Tsai et al. | |
| 5,980,704 A | 11/1999 | Cherukuri et al. | |
| 5,994,696 A | 11/1999 | Tai et al. | |
| 5,994,816 A | 11/1999 | Dhuler et al. | |
| 6,003,833 A | 12/1999 | Tasi et al. | |
| 6,007,208 A | 12/1999 | Dickensheets et al. | |
| 6,014,889 A | 1/2000 | Castor | |
| 6,016,686 A | 1/2000 | Thundat | |
| 6,023,961 A | 2/2000 | Discenzo et al. | |
| 6,032,527 A | 3/2000 | Genova et al. | |
| 6,033,131 A | 3/2000 | Ghosh et al. | |
| 6,033,544 A | 3/2000 | Demers et al. | |
| 6,037,704 A | 3/2000 | Welle | |
| 6,039,316 A | 3/2000 | Jackson et al. | |
| 6,040,935 A | 3/2000 | Michalicek | |
| 6,043,080 A | 3/2000 | Lipshutz et al. | |
| 6,054,277 A | 4/2000 | Furcht et al. | |
| 6,171,253 B1 | 1/2001 | Bullister et al. | |
| 2001/0055812 A1 | 12/2001 | Mian et al. | |

FOREIGN PATENT DOCUMENTS

| | | |
|---|---|---|
| DE | 2 390 173 | 8/1978 |
| EP | 0 096 217 | 12/1983 |
| EP | 0 165 751 | 12/1985 |
| EP | 0 214 803 | 3/1987 |
| GB | 2 176 717 | 1/1987 |
| WO | WO 88/01880 | 3/1988 |
| WO | WO 88/05691 | 8/1988 |
| WO | WO 93/10385 | 5/1993 |
| WO | WO 93/12888 | 7/1993 |
| WO | WO 94/11093 | 5/1994 |
| WO | WO 97/24915 | 7/1997 |
| WO | WO 97/42477 | 11/1997 |
| WO | WO 98/32616 | 7/1998 |
| WO | WO 99/26048 | 5/1999 |
| WO | WO 99/34383 | 7/1999 |
| WO | WO 99/53205 | 10/1999 |
| WO | WO 99/54199 | 10/1999 |

OTHER PUBLICATIONS

The Knowledge Foundation Inc., "Novel Microfabrication Options for BioMEMS Technologies & Commercialization Strategies," presented by The Knowledge Foundation Inc. in.

* cited by examiner

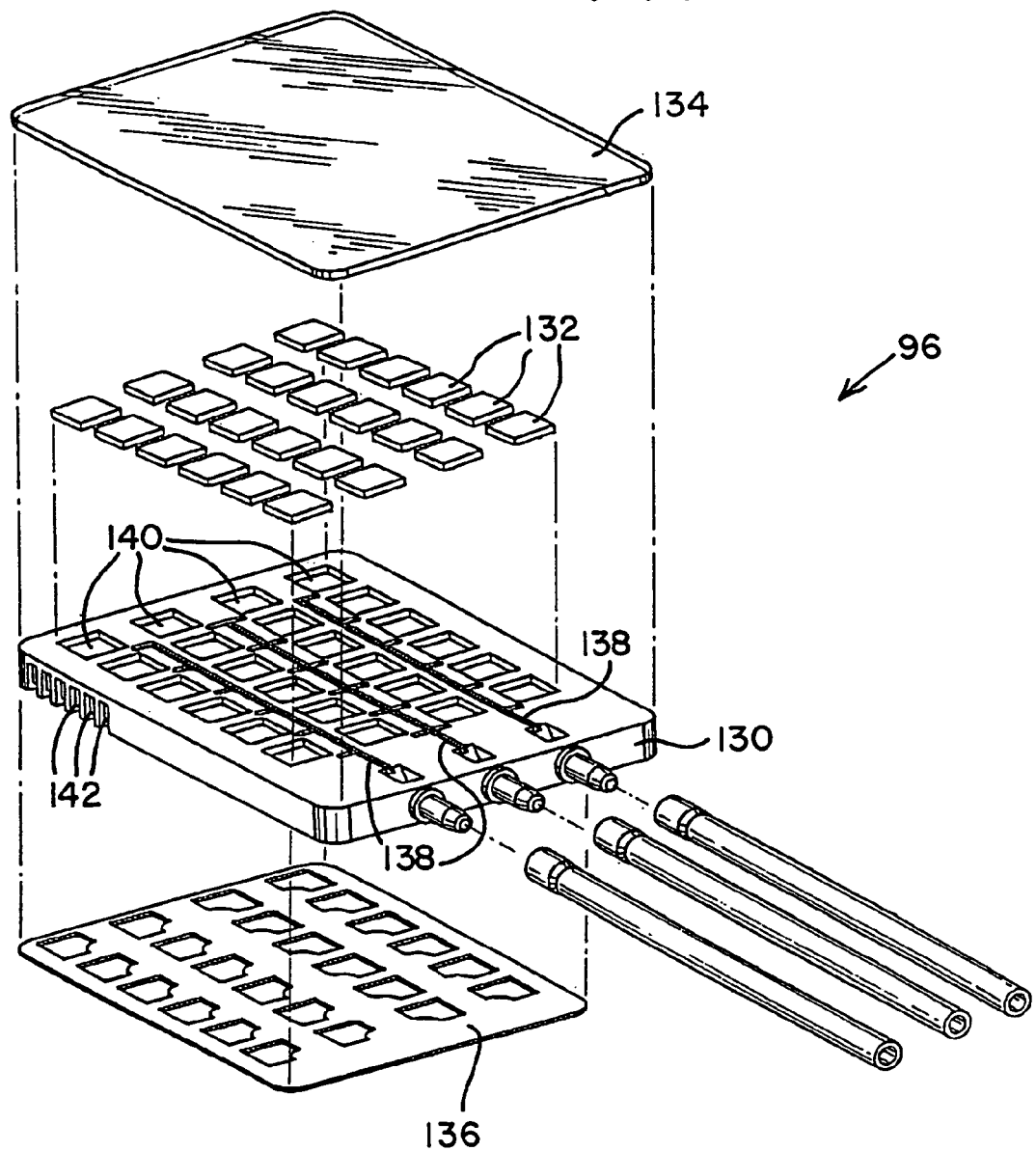

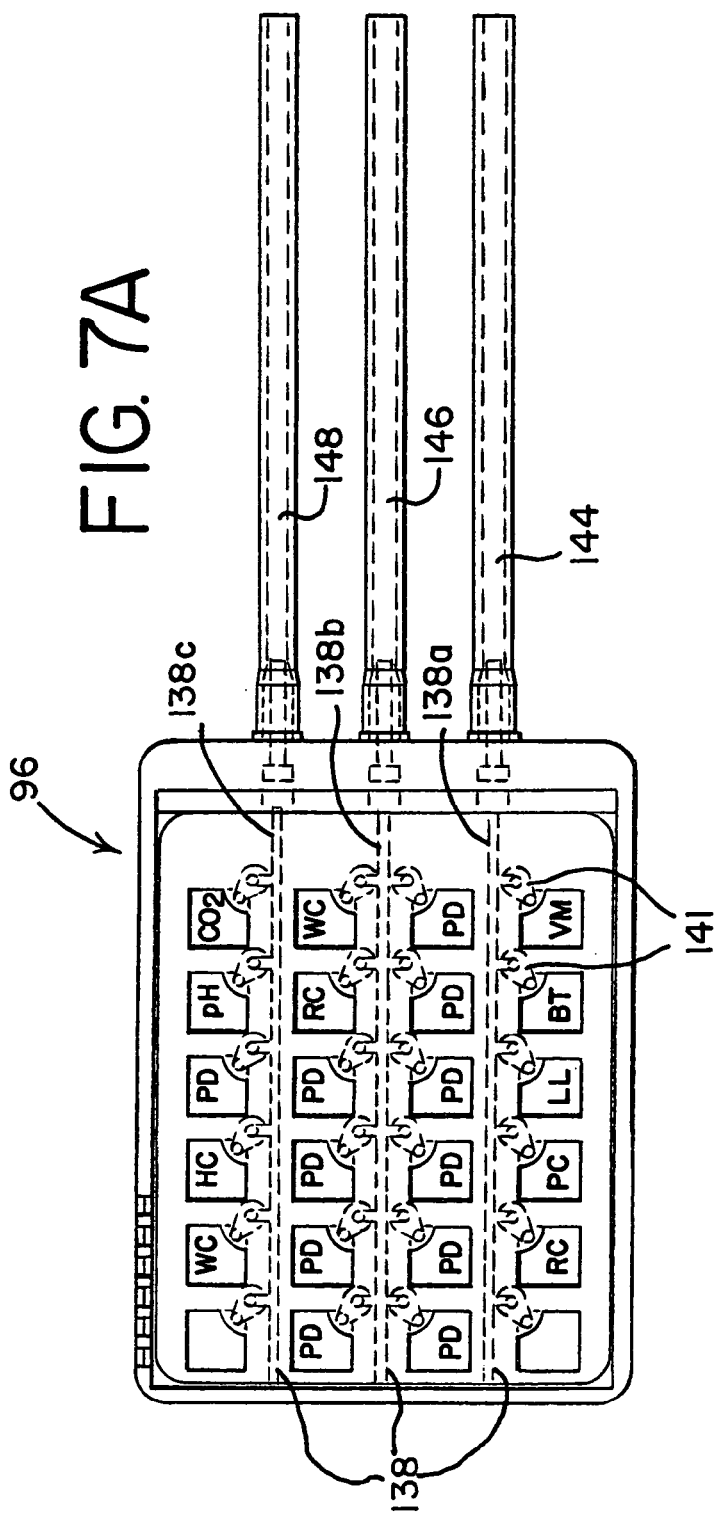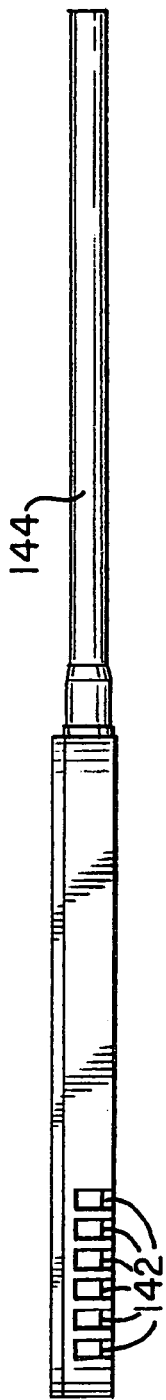

MEDICAL SYSTEM, METHOD AND APPARATUS EMPLOYING MEMS

RELATED APPLICATION

This application is a continuation of U.S. application Ser. No. 10/031,112 filed Jan. 14, 2002, now U.S. Pat. No. 6,994,781, entitled "Medical System, Method and Apparatus Employing MEMS," which was the National Stage of International Application No. PCT/US01/21188, filed Jul. 3, 2001, which claims the benefit of U.S. Provisional Application No. 60/216,640, filed Jul. 7, 2000.

The present invention relates generally to medical systems, methods and apparatus for processing biological suspensions including, but not limited to, blood. More specifically, the present invention relates to novel medical systems, methods and apparatus (for processing biological suspensions) that employ microelectromechanical systems ("MEMS") as sensors, detectors or other elements for improving product quality, purity, consistency, characterization, and/or production.

The present invention is described below in connection with the processing of blood and blood components, a field in which it is expected to find substantial application and benefit. However, it should be understood that the present invention is not limited to blood or blood component processing and may be employed in connection with the processing of other biological suspensions, for example, bone marrow or cell growth media.

The processing of blood and blood components has taken on increased significance in recent years due to the increased demand for blood and blood components for therapeutic application. Blood is a suspension of cells or cell fragments that are suspended in a liquid. The cells include red cells, for carrying oxygen from the lungs to the muscles and returning carbon dioxide from the muscles to the lungs, white cells, for fighting infection, and platelets, for clotting. The cells are suspended in a liquid called plasma, and the plasma itself has constituents that can be separated through a process called fractionation. For purposes of this description, blood "component" and blood "constituent" are used interchangeably.

Red cells are typically needed by patients suffering from significant blood loss. Platelets are required by many patients undergoing chemotherapy or radiation treatment, which reduces the ability of the body to make new bloods cells (and platelets are among the shortest-lived blood cell). Plasma may be administered to patients for a variety of reasons, or may be subjected to further fractionation to isolate and concentrate certain blood proteins.

As the demand for blood components has increased, it has become routine to separate collected blood into its constituent parts so that only the required constituent is given to the patient, and the other components or constituents remain available for other patients, or are returned to the donor. A term commonly used for separation of blood into one or more constituents is "apheresis." Apheresis may be done manually, after whole blood is collected, or it may be carried out in an automated or semi-automated procedure.

Automated apheresis typically employs a reusable device or instrument and a disposable, single use tubing set through which the blood flows for processing. The collected constituent, such as platelets, red cells or plasma, is typically withdrawn and directed to a storage container, or collected within a container inside the device, and the other blood constituents are either returned to the donor or separately withdrawn and stored for other uses. A variety of devices, based on different principles, have been used in automated apheresis. The most common devices are based on centrifugation principles, and separate the blood components based on their different densities. The CS-3000® and Amicus separators by Baxter Healthcare Corporation of Deerfield, Ill., and the Trima® and Spectra® separators by Gambro BCT of Lakewood, Colo., are examples of centrifugal blood separators or apheresis devices. The Autopheresis-C separator by Baxter Healthcare Corporation is another type of apheresis device. It operates on a principle of membrane separation using Taylor vortices, which is much different than the above-identified centrifugation devices. The present invention is not limited to a particular treatment device or principle of operation, and may be of significant benefit in any of these and other blood or suspension treatment devices.

In addition to collection of blood constituents from healthy donors, the same equipment and processes may be used therapeutically, to treat ill patients. For example, when it is believed that a patient may benefit by depleting the amount of white cells or by removing plasma, the same equipment used with donors may be used to collect those constituents from patients, returning the remainder of the blood to the patient. Blood processing as a therapeutic procedure for a wide variety of conditions has also grown in recent years.

Although blood constituent collection or depletion has been performed for many years, and advances have been made, there remain significant areas where further improvements are needed. One area where there is significant need for improvement is in reducing the potential for human error in the collection and testing of blood components. In a normal platelet collection procedure, for example, a number of tests are conducted on the blood withdrawn from the donor and on the platelet concentrate that is collected. For example, an incoming blood sample may be withdrawn from the tubing set and sent to a laboratory for testing regarding platelet count, the presence of pathogens, blood type, and a variety of other tests.

A sample of the collected blood constituent may also be subjected to similar tests. For platelets, for example, the amount of collected platelets is a particularly important number, because a certain amount of platelets ($4 \times 10^{11}$) is usually necessary to constitute a standard "dose" or "unit" of platelets. In addition to determining the number (or, alternatively, the density) of platelets collected, the collected platelet product also may be tested for the presence of white cells, which are a suggested source of adverse reactions in some patients.

Many of these tests either are not conducted at the same place the blood component is collected or require 24–48 hours to complete. Great care must be taken, and numerous administrative steps completed, to assure that the sample is properly traceable to the collected blood product, and that the laboratory results are properly recorded in connection with the particular blood product collected. Notwithstanding such care, because of the number of individuals and steps involved, the risk of human error in this process is real, even if small. Accordingly there is a continuing need for advances that reduce the amount of human handling and intervention required, and thus the potential for error as well as the cost associated with collecting and testing blood constituents. More specifically, there is a need for collection or treatment systems that provide a product, such as blood platelets, red cells or plasma, which is fully or partially characterized, such as by cell count, pathogen presence, white cell count, blood type, et cetera, with minimum human intervention and with minimum need for testing procedures that separate the testing from the treatment process itself and thereby introduce opportunity for human error.

Because the demand for blood components is not constant, it also is not unusual for certain blood constituents to be wasted due to outdating before they are used. Although red cells, which may be refrigerated and stored for lengthier periods of time, blood platelets are normally stored at room temperature, and have a limited shelf life of about 5–7 days under the best of circumstances. Both, however, have limited shelf life, and, as a result, it is not uncommon for a significant amount of collected blood constituent product to be wasted because it is not used within the allowed shelf life period. Thus, in light of the limited donor pool that is available to contribute platelets and other blood components, there is a need for better efficiencies in collecting and using blood components.

In addition to the above, there is a continuing need for devices that make the collection process itself more efficient. For example, the hematocrit and platelet count of a donor may be of significant value in tailoring or optimizing the collection procedure to obtain the desired amount of the collected product, in the desired amount of time, with the desired amount of purity or freedom from undesirable components, and with minimum adverse effects to the donor or patient. Although the donor's hematocrit may be measured reasonably easily prior to a collection procedure, platelet count is an expensive and time consuming procedure, and typically is not done prior to the procedure. In most platelet collection procedures, the best available information is an estimated platelet count, based on an average of prior donations, which can vary widely. Accordingly, there is a need for more current information that can be used to optimize the collection procedure.

In summary, there is a continuing need for improvement in providing blood constituents regarding (1) the consistency of the collected product, for example in terms of the yield or amount of constituent collected and available for transfusion or the quality (e.g., viability) of the blood constituent collected, (2) the purity of the collected product, for example the absence of undesirable contaminants and better assurance of completion of all the necessary testing with reduced chance of human error, (3) the efficiency of collection and usage of collected blood constituent, (4) the cost and error potential in the collection and associated testing and administrative burden and (5) the safety afforded to the donor.

Within the past decade significant progress has also been made in the field of microelectromechanical systems (MEMS). MEMS is a class of systems that are physically very, very small. These systems typically, but not exclusively, have both electrical and mechanical or optical components. Modified integrated circuit fabrication techniques and materials were originally used to create these very small devices or systems, but currently many more fabrication techniques and materials are available.

MEMS devices have been conceived for a variety of sensing and actuating functions. MEMS devices have been conceived for typing blood, counting cells, identifying DNA, performing chemical assays, measuring pH, sensing partial pressures, and performing a wide variety of other procedures and tests. Recently, various manufacturers have even claimed to have developed a "lab on a chip" that is suitable for carrying out a variety of blood or blood constituent assays or tests. However, progress in integrating MEMS devices into pre-existing medical procedures to enhance performance and reduce potential for human error has been limited.

SUMMARY

To achieve one or more of the above objectives, the present invention employs a MEMS sensor in a system for processing a biological suspension, for example blood, in a treatment device, wherein the MEMS sensor is employed to sense one or more fluid characteristics of fluid flowing into or from the treatment device. More specifically, the present invention may be embodied in a biological suspension processing system comprising a suspension treatment device for treating one or more components of a biological suspension, a first fluid flow path communicating with the treatment device for introducing a suspension into the treatment device, and a second fluid flow path communicating with the treatment device for withdrawing a constituent of the suspension from the treatment device. In accordance with the present invention, at least one microelectromechanical (MEMS) sensor communicates with one of said fluid flow paths for sensing a selected characteristic of the fluid within the flow path. The treatment device may be an apheresis device for separating and collecting one or more blood constituents, but in its broader aspects, the present invention is not necessarily limited to a particular suspension treatment device or to a particular apheresis device or separator.

Turning back to aspects of the present invention, the MEMS sensor may be operable to sense a characteristic such as, for example, one of those selected from the group consisting of flow rate, pH, cell type, cell antigenicity, cell concentration, cell count, viscosity, cholesterol, hematocrit, DNA, viral or bacterial presence, pathogen presence, and/or partial pressure of a selected gas or other characteristics.

To aid in control of the system, the sensor may communicate with the first fluid flow path and generate a signal responsive to one or more selected characteristics of the fluid (e.g. platelet count) in the first fluid flow path. The suspension treatment device may include a controller adapted to receive the sensor signal and to control the treatment device in response to the signal. This system could be used, for example, to optimize the treatment procedure time, to provide a more consistent product, to provide a product that has a certain minimum quantity of suspension constituent, or to better safeguard patient affects. A sensor may also communicate with the second fluid flow path, which conducts the fluid being withdrawn from the treatment device, for example to count desired or non-desired components, such as platelets or white cells, or for other desired purposes.

For even better control the system may include sensor adapted to sense a selected characteristic a plurality of times at discrete intervals. This sensor may generate a signal each time it senses the characteristic, and the suspension treatment device may include a controller that is adapted to receive the sensor signal and to control the treatment device in response thereto. Thus, periodic sensing may be used to better optimize or improve the treatment procedure over all or part of the treatment procedure. For example, the sensor may communicate with the second fluid flow path and sense the approximate quantity or concentration of a selected cell, with the controller controlling the system to collect a desired quantity of the selected cell, or alternatively, to reduce the collected amount of the selected cell.

The system may further comprise a container communicating with the second fluid flow path for receiving the withdrawn constituent, with the system being adapted to provide tracking information for associating with the container the particular characteristic sensed by at least one sensor. A machine readable or human readable data storage media may be carried by the container to store information regarding the particular characteristics sensed by at least one sensor. The data storage media is not limited to a particular type, and may comprises a graphic indicator such as a bar code label on the container, an electronic data storage device, such as one with a non-volatile semiconductor memory, or an icon or other graphic carried by the container representative of the sensed characteristic. This tracking may be entirely carried out by the system, thereby reducing the possibility of human error in mishandling of the sample or information.

When the suspension includes one or more blood components and the blood component withdrawn is a cellular component, the system may include a container for storing the cellular component withdrawn, and the data storage media may include data regarding, for example, the type, quality, purity, quantity and/or concentration of the cellular component in the container. More specifically, the system may include a first sensor communicating with the first fluid flow path and a second sensor communicating with the second flow path and the treatment device may comprise an apheresis device. When the suspension comprises whole blood, the first sensor may sense inter alia, platelets to determine a platelet count in the suspension introduced into the apheresis device and the second sensor may sense inter alia, platelets withdrawn to determine a platelet count in the second flow path. A container communicating with the second flow path may be provided to store the blood platelets withdrawn, and the system may further comprises machine readable or human readable data storage media carried by the container for storing information regarding platelet count sensed by one or both of said sensors. To reduce the number of human interventions required, the system may itself include a data recording device for receiving a signal from one or more of the sensors and recording the data regarding the sensed characteristic. The data recording device may be a printer for printing a human or machine readable report of the characteristic sensed, such as directly on the container or on a label affixed to the container. Alternatively, the container may carry a machine readable electronic data storage device, and the data recording device be adapted to transfer data regarding the selected characteristic sensed by the sensor to the electronic data storage device. An electronic data storage device may preferably comprise a non-volatile semiconductor memory, or "write once, reads many times" memory so that the data is not inadvertently lost or destroyed by power loss. In other words, a memory or processing chip may be added to the blood constituent storage container, such as permanently mounted in the tail flap of the container, with a non-volatile memory, for receiving and storing data for later access by the appropriate electronic reading instrument.

The blood component storage container also may include a microelectromechanical sensor carried by the container and communicating with the container compartment for sensing a selected characteristic, for example just before administration to a patient, of the blood component received or stored therein. Such a sensor similarly may include a non-volatile semiconductor memory or so-called "write once, read many times" data storage.

In accordance with another aspect, the present invention may be directed to a blood processing system for providing a characterized blood constituent product in which the system comprises: an apheresis device for separating one or more desired cellular blood constituents from a suspension comprising whole blood, a first fluid flow path communicating with the apheresis device for introducing a suspension comprising whole blood into the device, a second fluid flow path communicating with the apheresis device for withdrawing at least one desired cellular blood constituent from the device, a container communicating with the second fluid flow path for receiving the blood constituent withdrawn from the apheresis device, machine readable or human readable data storage media carried by the container, at least one microelectromechanical sensor communicating with the first fluid flow path for sensing at least one characteristic of the whole blood and for generating at least one electrical signal responsive to such sensing, at least one microelectromechanical sensor communicating with the second flow path for sensing the quantity of cellular blood constituent withdrawn from the apheresis device and for generating an electrical signal responsive to such sensing, a data recorder adapted to receive the electrical signals from the sensors and to record data regarding the sensed characteristics on the data storage media, whereby a user may readily identify the sensed characteristic regarding the whole blood and the quantity of the desired cellular constituent in the container with a minimum of human intervention.

This system may further include a sensor communicating with the second fluid flow path for sensing the quantity of a non-desired biologic constituent in the flow path and generating an electrical signal responsive to the quantity, the data recorder being adapted to receive such signal and record data regarding the quantity of non-desired cellular constituent in the data storage media for access by a user of the product in the container. The non-desired biologic component may be a viral constituent, or a cellular constituent, such as white cells.

As before, the system may include a controller adapted to receive the signals from the sensors communicating with the first and second fluid flow paths and to control the apheresis device in response to one or more of such signals to provide a desired cellular blood constituent product characterized by data recorded in the data storage media in accordance with characteristics sensed by the sensors. The data storage media may comprise machine readable graphics carried on the container, for example, a bar code. The system may also, when withdrawing blood from a donor or patient, for example, generate a human-readable report for the donor or patient containing selected data regarding one or more of the sensed characteristics.

In accordance with another aspect of the present invention, a biological suspension processing system may be provided which includes: a blood treatment device for treating one or more components of a biological suspension, a human subject, a first fluid flow path communicating with the vascular system of the human subject and the treatment device for introducing blood from the human subject into the treatment device, a second fluid flow path communicating with the treatment device for withdrawing a constituent of the blood from the treatment device, a third fluid flow path communicating with the treatment device from withdrawing another constituent of the blood from the treatment device, and at least one microelectromechanical sensor communicating with one of said fluid flow paths for sensing a selected characteristic of the fluid within the flow path.

The sensor may generate a signal responsive to one or more selected characteristic of the fluid in one of the fluid flow path, with the suspension treatment device including a controller adapted to receive the sensor signal and to control the treatment device in response thereto. In the situation where the third fluid flow path communicates with the human subject, and the treatment device is adapted to add anticoagulant to the blood in the first fluid flow path, the selected characteristic may include the hematocrit of blood in the first fluid flow path. In that setting, the controller may control the addition of anticoagulant into the first fluid flow path to prevent too much anticoagulant from being returned to the donor or patient, because, as is well known excess anticoagulant flow to the donor or patient may have deleterious consequences.

The signal from the sensor and the control of the treatment device is not limited, however, to the safety of the human subject. The controller may, for example, in response to the signal control the treatment device to withdraw a constituent of desired quality, to withdraw a constituent of desired quantity, to withdraw a constituent that is depleted of an undesired component, or to withdraw a selected minimum quantity of constituents, such as platelets, red cells or plasma, or to withdraw a certain amount of constituent in a maximum or minimum procedure time.

In a more specific embodiment of the present invention, the MEMS sensor(s) or other MEMS devices are located on a common disposable carrier or cassette. The carrier includes internally defined fluid flow passageways that may be selectively opened or closed by macro or MEMS scale valves to control flow of fluid to the sensors in response to control signals from the device controller. The carrier is preferably adapted to interfit with a reusable reader/controller which cooperates with the MEMS devices located in the cassette to provide a signal responsive to the sensed characteristic, which signal may be used to optimize the treatment procedure or to identify the sensed characteristic for later association with or labeling of the collected blood product, or to control the flow of fluid through the cassette.

Although the carrier may take several different forms, in one form of a cassette, it is comprised of a rigid plastic base that mounts a plurality of MEMS sensors or other MEMS devices such as valves or pumps, and has preformed passageways defined in the base with fluid flow control valve modules located to control the flow of selected fluid to the desired MEMS sensor. The cassette may include preformed open passageways that are closed by a resilient membrane which overlies one side of the cassette and is sealed to the passageway walls (either temporarily by pressure exerted by the reader or permanently by solvent or sonic bonding) to close the passageways. The membrane may cooperate, such as by mechanical or pneumatic actuation, with the valve modules to control the flow of fluid through passageways in the MEMS cassette.

The present invention is not limited to a particular type of MEMS sensor or to a particular principle of operation. The MEMS devices useful in the present invention may be static or dynamic, purely mechanical, biomechanical or electro-mechanical. They may also include optical components, and they may be dry or used in combination with liquid reagents or other liquids.

One type of MEMS sensor that holds promise for apheresis procedures is a microcytometer in which particles, for example cells, or cell fragments, are fed through a narrow, microfluidic channel in single file. Other MEMS sensors may be based, for example, on centrifugal microfluidics analysis employing a rotating compact disc that employs, for example, a micro-fluidics manifold and spectrophotometric cuvette formed on the surface of the disc, which may be read by an optical disc reader.

Because certain MEMS devices may require special or separate sterilization procedures as compared to other MEMS devices, the present invention also contemplates that there may be more than one MEMS carrier or cassette. For example, MEMS employing reagents may require a different sterilization technique, such as ethylene oxide sterilization, as compared to purely mechanical or electro/mechanical, optical/mechanical or optical/electrical MEMS devices, which may be suitable for radiation or heat sterilization. There may also be other reasons for having more than one MEMS cassette, including ease of manufacturing, ease of mounting or assembly on the treatment device, and the like. In such case, the MEMS cassette may be attached to the remainder of the fluid circuit after sterilization, as by sterile docking or other sterile connection procedure.

Fluid may be pumped through the MEMS cassette by the peristaltic pumps that are typically employed on apheresis devices for moving blood and blood components through the tubing set or, alternatively, the MEMS cassette itself may include macro and/or MEMS-scale pumps for circulating fluid through the MEMS cassette, and to the desired MEMS sensor. Similarly, liquid flow through the cassette may be controlled by MEMS scale valves, or by macro scale valves such as those employed in the fluid flow control modules of the Amicus apheresis centrifuge marketed by Baxter Healthcare.

Additional aspects and features of the present invention are set forth in the following detailed description.

BRIEF DESCRIPTION OF THE DRAWINGS

FIG. 6 is an exploded perspective view of a MEMS cassette or carrier that may be used in the disposable fluid circuit of FIG. 5, embodying the present invention.

FIG. 7a is a top view of the assembled MEMS cassette of FIG. 6.

FIG. 7b is a side view of the MEMS cassette of FIG. 7a.

FIG. 17b is an elevational view of a reader for the compact disc of FIG. 17a.

DETAILED DESCRIPTION OF DRAWINGS

Figure 1:
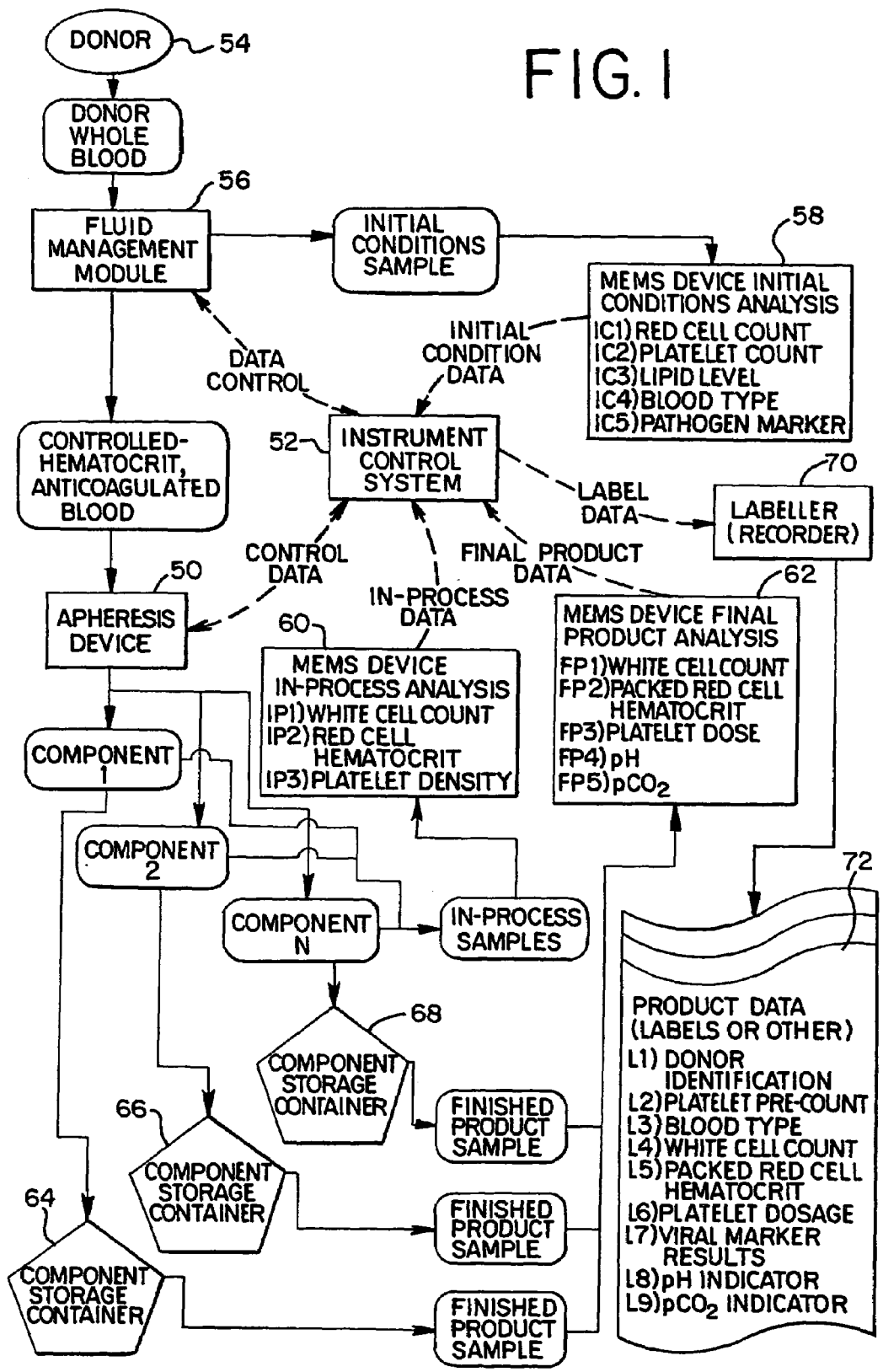
FIG. 1 is schematic flow chart of a suspension treatment system embodying the present invention.

Turning now to a more detailed description of the drawings, FIG. 1 is a flow chart illustrating a treatment system embodying the present invention. Although the flow chart in FIG. 1 is in the context of a blood apheresis system, the flow chart and the steps indicated therein have application to other suspension treatment systems as well.

Before describing the treatment system in more detail, it should be understood that the flow chart is intended to reflect general system features and functions, and not necessarily the system structure. For example, it should be understood that features shown in a single box or grouping of the flow chart may represent what are actually two or more physical modules or structures in the actual product, and more than one box or grouping in the flow chart may be a single physical module or structure in the final product. The purpose of the flow chart is simply to illustrate one embodiment of an overall system and function, and not to limit the actual physical structure.

As applied to apheresis, the system in FIG. 1 includes an apheresis device 50, such as a centrifuge, spinning membrane separator or other apheresis device or instrument, and an instrument or device control system 52. The control system 52, which may comprise a programmable microprocessor, performs a variety of control and monitoring functions for carrying out an apheresis procedure. It receives and sends data regarding various initial, in-process and final product characteristics, it controls the fluid flow through the system, it controls the operation of the apheresis device and it tracks and stores data for labeling the final product or for communicating with data storage media associated with the container in which product is collected during the apheresis procedure.

In the system shown in FIG. 1, whole blood is collected from a donor 54, such as a healthy adult human. The flow of blood (and other liquids such as priming solution and anticoagulant) through the system is controlled by a fluid management module 56. In accordance with the present invention, one or more characteristics of the blood flowing into the system may be sensed by one or more MEMS sensors. For example, an initial sample of the whole blood, before processing, may brought into contact with one or more initial condition MEMS sensors 58 for sensing or measuring red cell count, platelet count, lipid level, blood type or markers representative of pathogen (viral or bacteria) presence. As used here, "sensor" or "sensing" is used broadly, and includes detecting, measuring, monitoring, analyzing, characterizing, sampling and any other tests or analysis that may be desired.

Data from the initial conditional sampling, typically in the form of an electrical signal, may be fed back to the control system 52 for purposes, for example, of controlling the fluid management module or the apheresis separation process or for tracking or storing information relating to the sensed characteristic for later association with the collected product. For example, data as to blood type may be saved for recording on a machine readable or human readable data storage media carried by the container for the collected product, such as a descriptive label, bar code or electronic memory device. Data regarding initial platelet count may be used, for example, to optimize the apheresis procedure to minimize procedure time, to maximize the amount of platelets collected or to better assure collection of a certain minimum number of platelets.

The anticoagulated whole blood is directed by the fluid management module to the apheresis device or instrument 50. There, the blood is separated into one or more components, such as components nos. 1, 2 and up to "n" components. During the apheresis procedure, in-process data may be sensed by one or more of the in-process condition MEMS sensors 60, for detecting characteristics such as white cell count, red cell hematocrit and platelet density. Data from the in-process condition MEMS sensor(s) may be fed back to the control system 52, typically for controlling the apheresis process and/or fluid flow. The in-process condition MEMS sensor may sample fluid one or more times during the procedure, as desired. To provide periodic adjustment of the apheresis device or fluid flow throughout the apheresis procedure, a plurality of MEMS sensors may be employed in the in-process sensing. These MEMS sensors may be activated by the control system to sense one or more selected characteristic at selected time intervals throughout the procedure or upon occurrence of certain triggering events, such as power outage, red cell spill over or other event.

The separated blood components not returned to the donor are directed to storage containers 64, 66 and 68, respectively. It is not necessary, of course, for the storage containers to be outside of the apheresis device. In the Baxter CS-3000® and Amicus® centrifuges, for example, blood components may be collected in containers that reside inside the rotating centrifuge until the apheresis procedure is completed.

As one or more components are collected, one or more characteristics of the final collected product may be sensed by the MEMS final product condition sensor(s) 62 and data relayed back to the controller 52. The final product condition MEMS sensor 62 may be provided to sense one or more characteristics of the collected product, such as white cell count, packed red cell hematocrit, platelet dose, pH, or gas (e.g., $CO_2$) partial pressure. The final product condition MEMS may feed data back to the control system 52 for optimizing the apheresis procedure, controlling fluid flow and/or storing/tracking data for association with the final collected product.

One of the benefits of certain aspects of the present invention is the providing of a final product that is fully or partially characterized according to the initial condition, in-process and/or final product condition MEMS sensors, with the characteristics sensed being tracked or stored for association with the final product container, all occurring with reduced human intervention and opportunity for error. For example, having received data from the various MEMS condition sensors 58, 60 and 62, the instrument control system 52 may relay that data to a recorder or labeler 70, which records the data onto data storage media 72 carried by the storage container. The data or storage media may be human readable, or machine readable (e.g., graphic or bar code), or a combination of both or other form. The recorder may, for example, print a label for attachment to the container, or transfer the data to a machine readable electronic storage device, such as a memory chip, carried by the container. The result is a blood component product characterized as needed, with reduced need for human intervention or opportunity for human error.

Figure 2:
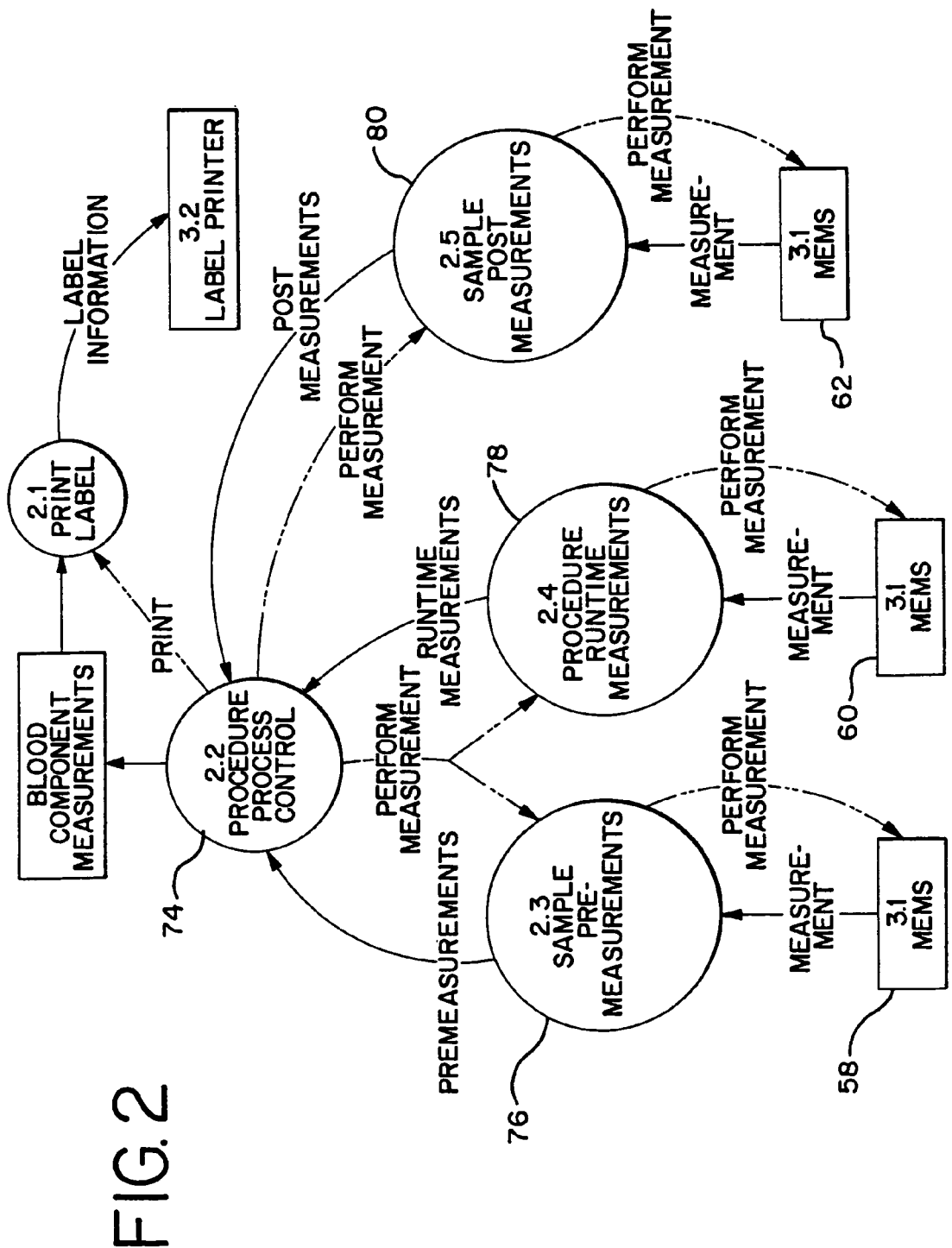
FIG. 2 is a software/data flow chart for a control and data flow system that may be employed in the present invention.

FIG. 2 is an outline of certain aspects of a programmable operation control system. As shown there, the procedure process master control module 74 may instruct (shown by dashed lines) various elements of the system to perform certain functions, and receive (shown by solid lines) data from one or more of those elements. For example, the master control may direct the sample pre-measurement module 76 to carry out certain initial condition sensing. This may be carried out by opening a macro or MEMS-scale valve that directs incoming whole blood into contact with the desired initial condition MEMS sensor 58. The information or data regarding the sensed characteristic is then relayed back through the pre-measurement module to the master control module for storage or for later association with the collected blood product.

Similar steps may be carried out as between the master control module 74 and the in-process module 78 and in-process MEMS sensor(s) 60, and as between the master control module and the final product configuration module 80 and final product condition sensor(s) 62.

Information from the various MEMS sensors may then be relayed to the recorder/labeler 70 for associating the data with the final product container. In one simple form, this may be by way of printing a label for attachment to the container or for printing the desired information on a pre-attached label, although the present invention also contemplates that data could be transferred optically or electrically to an electronic data storage device (such as a non-volatile memory chip or "write once, read many times" storage device) attached to the final product container. If the operator desires that only certain information be displayed with the product, the system permits less than all of the characteristics that are sensed to be displayed on or in connection with the collected product.

Figure 3:
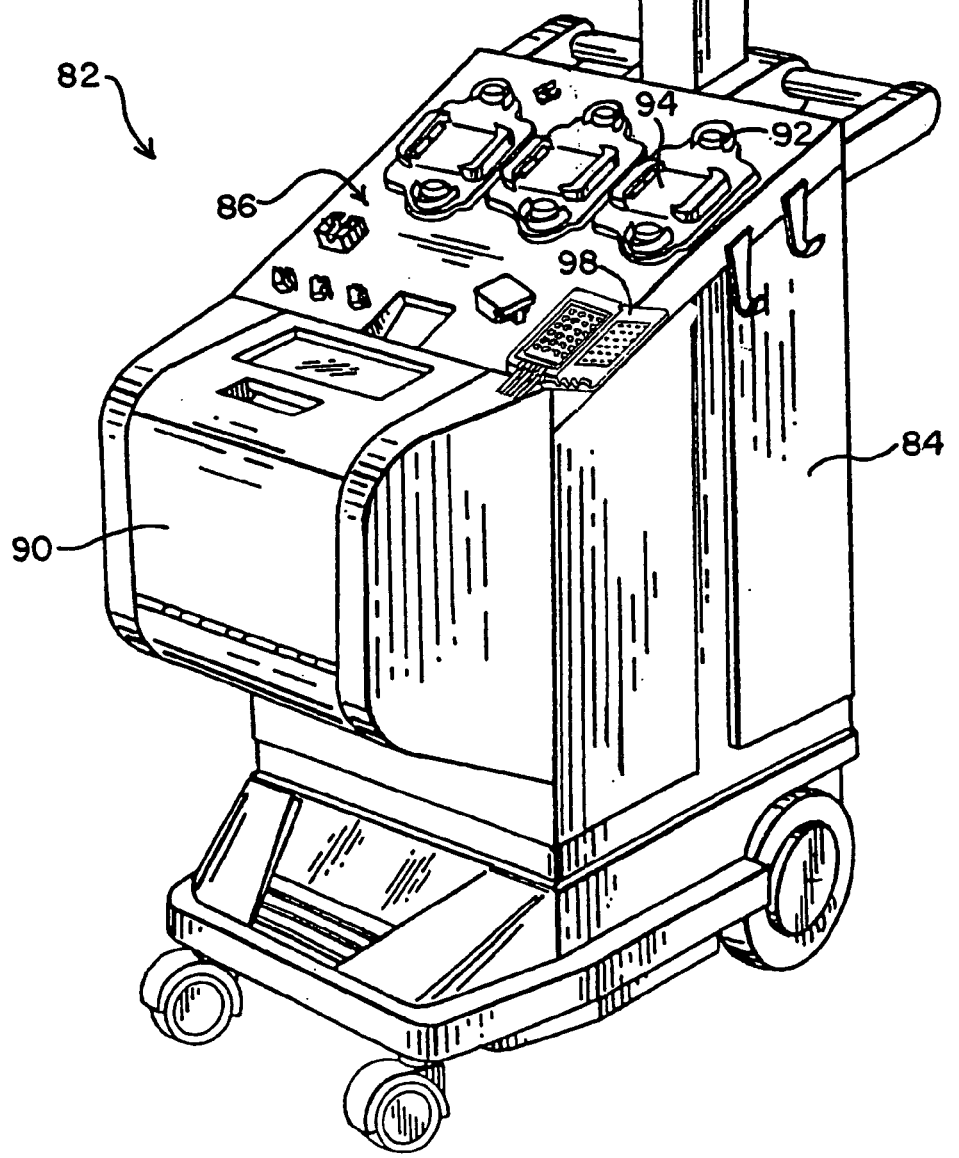
FIG. 3 is a perspective view of a reusable suspension treatment device, specifically an apheresis device, embodying the present invention.

FIG. 3 shows a biological suspension treatment device, and specifically an Amicus® apheresis instrument 82 of the general type made and sold by Baxter Healthcare Corporation of Deerfield, Ill. The Amicus® separator is described in detail in U.S. Pat. No. 5,462,416, which is incorporated by reference, and that description will not be repeated in full here.

Briefly, the Amicus® separator is based on centrifugation principles, and separates blood components by reason of their different densities. The Amicus® separator is intended to work with a disposable, one-time use plastic tubing set, which will be described later, through which blood and blood components flow during the apheresis procedure.

The Amicus® separator includes a base portion, generally at 84, a fluid management and sensor panel area 86, and a display screen and touch control panel 88. The machine base 84 contains the rotating centrifuge chamber drive hardware and control electronics. The centrifuge chamber is accessible through a drop-down front door 90 for loading and removing the disposable tubing set.

The fluid management and sensor panel includes three pump and valve stations, each of which has a pair of peristaltic pumps 92 and adjacent flow control module 94 for pumping fluid through the system and controlling the direction of fluid flow. User information regarding the apheresis-procedure is displayed on the display screen 88, which also includes touch input capability for operator entry of information or control commands prior to and during the apheresis procedure.

In accordance with a preferred version of the present invention, the MEMS sensors and other devices are mounted on a single MEMS carrier or cassette 96 (FIG. 5), which is part of the disposable fluid circuit and intended for one-time use only. The apheresis instrument 82 (FIG. 3) includes a MEMS cassette reader/controller 98 into which the MEMS cassette is mounted when the disposable fluid circuit is installed on the instrument. The reader/actuator 98 cooperates with the MEMS cassette for reading or transferring data from the MEMS sensors on the cassette and for controlling flow of fluid through the MEMS cassette and to the desired MEMS sensor or other MEMS device.

Figure 4:
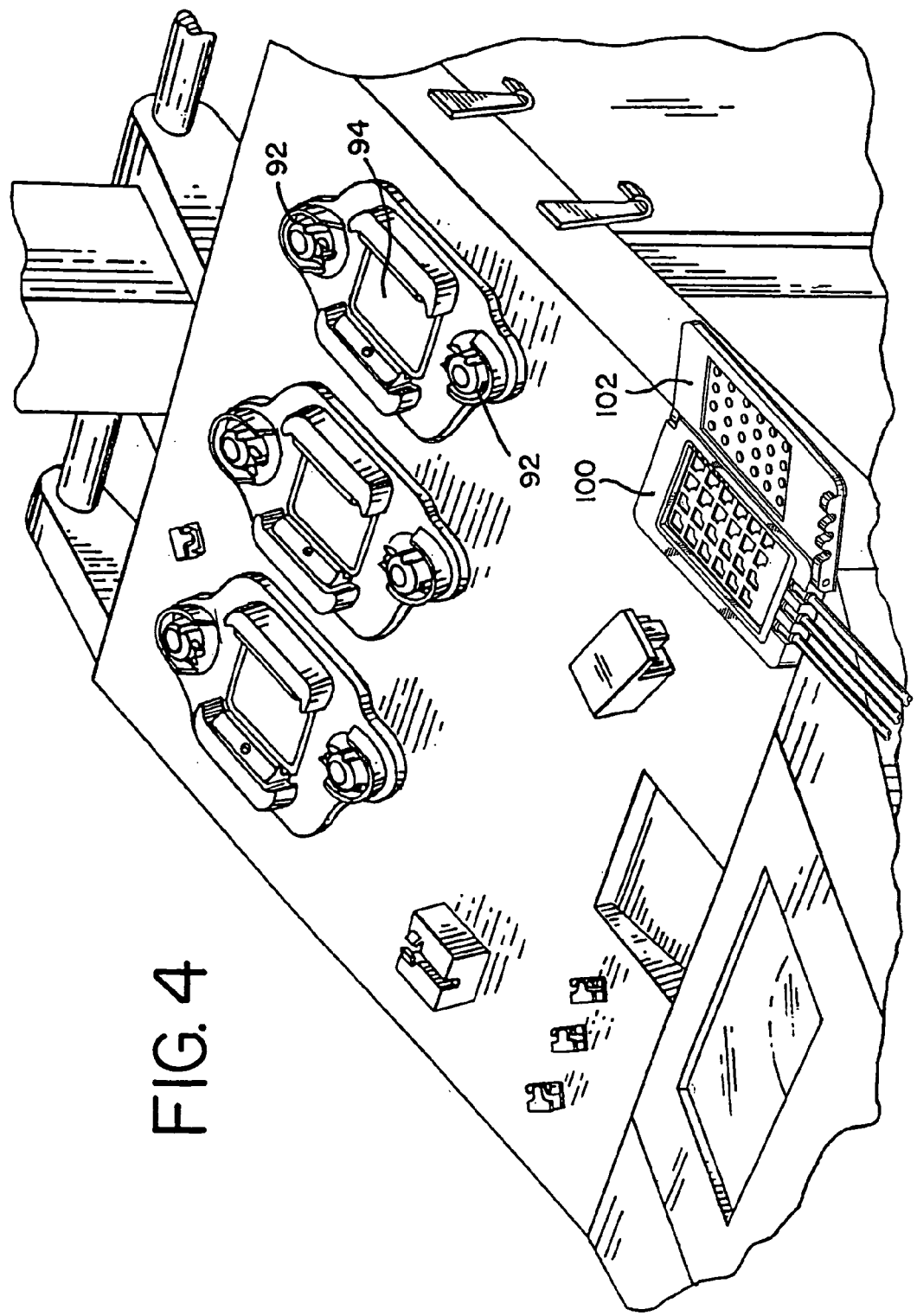
FIG. 4 is an enlarged perspective view of a portion of the device of FIG. 3, showing the reader/controller for a MEMS cassette or carrier.

The MEMS cassette reader/controller shown in FIG. 3, and shown in larger view in FIG. 4, employs a base 100 adapted to receive the MEMS cassette and a door 102 pivotally mounted on the base for closing over the cassette to block out ambient light and cooperate with optical, electronic or mechanical devices located in the base portion for reading or interpreting the MEMS sensors or other devices and/or for actuating valves or pumps located in the MEMS cassette.

Figure 5:
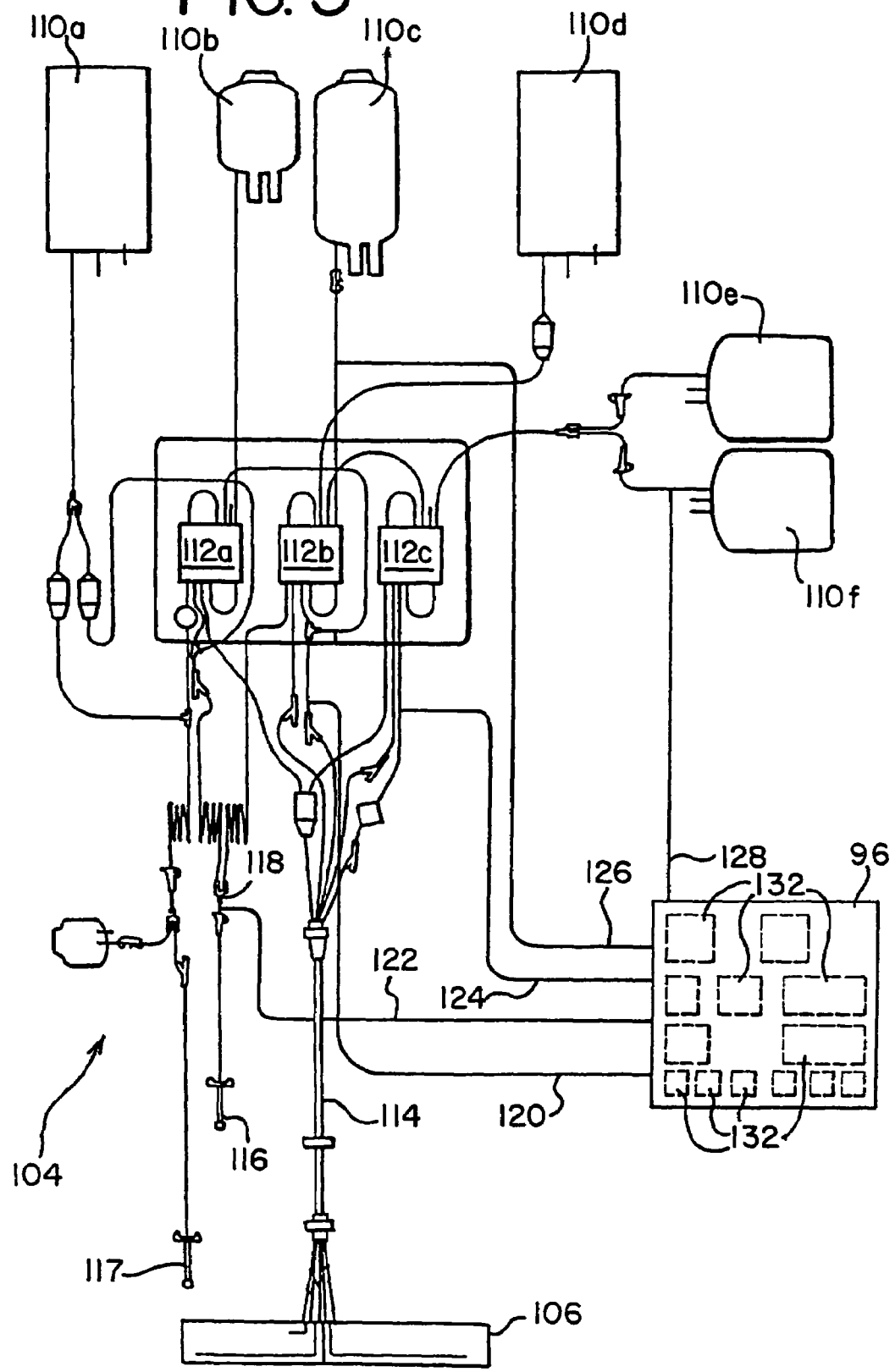
FIG. 5 is a plan schematic of a disposable fluid circuit, including a MEMS cassette or carrier, for use with the device of FIG. 3 and employing the present invention.

FIG. 5 is a schematic view of a disposable one-time-use processing assembly or fluid circuit 104 embodying the MEMS cassette/carrier 96 of the present invention for use on the apheresis instrument shown in FIG. 3. A detailed description of the disposable fluid circuit may be found in U.S. Pat. No. 5,462,416, which was previously incorporated by reference, and will not be repeated here.

The processing assembly 104 includes an array of flexible tubing that forms the fluid circuit through which blood and blood components flow. The fluid circuit conveys liquid to and from a processing chamber 106 that is mounted in the rotating centrifuge chamber during use. The fluid circuit includes a number of containers 110*a*–*f* that fit on hangers on the centrifuge assembly to dispense and receive liquids during the apheresis process.

The fluid circuit 104 also includes one or more in-line fluid control cassettes 112, which are not to be confused with the MEMS cassette (although the fluid control cassettes could also include MEMS sensors or other MEMS devices and thus incorporate features of the present invention, if desired). FIG. 5 shows three such cassettes designated 112*a*, 112*b* and 112*c*. The cassettes serve in association with the pump and valve stations on the centrifuge assembly to direct liquid flow among the multiple liquid sources and destinations. During a blood processing procedure the cassettes centralize the valving and pumping functions to carry out the selected procedure. Further details of these functions are described in the above mentioned U.S. Pat. No. 4,562,416.

A portion of the fluid circuit 108 leading between the cassettes 112*a*–*c* and the processing chamber 106 is bundled together to form an umbilicus 114. The umbilicus links the rotating parts of the processing assembly (principally the fluid management processing chamber) with the non-rotating, stationary parts of the processing assembly (principally the cassettes and containers and fluid circuit tubing and MEMS carrier or cassette). The umbilicus links the rotating and stationary parts of the processing assembly without using rotating seals, by employing the well known one-omega two-omega principle, which has long been successfully used in the CS-3000® centrifuge marketed by Baxter Healthcare Corporation.

In the illustrated and preferred embodiment, the fluid circuit 104 pre-connects the processing chamber 106, the containers 110, the fluid control cassettes 112 and the MEMS carrier/cassette 96. The assembly thereby preferably forms an integral pre-assembled sterile unit, although it is recognized that if separate sterilization is required for the MEMS cassette, it may require subsequent attachment, such as by sterile connection procedure, to the remainder of the fluid circuit.

During a typical dual needle platelet collection procedure, whole blood is drawn into an inlet needle 116 and combined at a junction 118 with anticoagulant such as ACD, which is pumped from the ACD container 110d, through fluid control cassette 112a and from there into the separation/processing chamber 106. In the separation chamber, platelet rich plasma is separated from packed red cells, and each is withdrawn from the separation chamber. The platelet rich plasma is withdrawn through the umbilicus 114 upwardly through cassette 112c and then, after passing through an optical sensor 120, returned to a collection chamber in the centrifuge. There, platelet concentrate is separated from the platelet rich plasma, and platelet-depleted or platelet-poor plasma is withdrawn from the collection chamber and collected in a platelet-poor plasma storage container 110c and/or returned to the donor, with red cells through fluid control cassette 112a and return needle 117. Although illustrated as a dual needle set, the present invention is equally applicable for a single needle fluid circuit of the type also previously sold by Baxter Healthcare Corporation for use on the Amicus® centrifuge.

In accordance with the present invention, as illustrated in FIG. 5, the fluid circuit 104 includes at least one MEMS cassette or carrier 96. As shown in FIG. 5 for purposes of illustration and not limitation, the MEMS cassette 96 is shown having five fluid connections. The number of connections, however, depends on the fluid characteristics to be sensed, and fewer fluid connections may suffice for many blood-related applications, as will be discussed later.

As illustrated in FIG. 5, the MEMS cassette 98 has a fluid inlet 120 connected to the packed red cell line. Fluid in this line may be monitored by MEMS sensors to determine the packed red cell hematocrit for the purpose, for example, of optimizing the separation procedure.

MEMS cassette fluid inlet 122 is connected to the whole blood inlet line. Fluid from this line may be sensed by MEMS sensors, for example, to determine any of the initial condition data such as red cell count, platelet count, lipid level, blood type or the presence of a pathogen (viral or bacteria) indicator or marker.

The next fluid entry inlet line 124, is shown communicating to the platelet rich plasma line. This may be used to perform in-process analysis of white cell count, red cell hematocrit, platelet density and the like.

Fluid connection 126 is connected to the platelet-depleted plasma line. MEMS sensors associated with this connection may be used to sense any of the desired final product characteristics of the plasma. Similarly, fluid connection 128 is attached to the platelet concentrate collection tubing for MEMS sensing of one or more of the final characteristics of the platelet concentrate, such as platelet dose or density, white cell count, platelet size, and the like.

A MEMS cassette or carrier 98 as presently contemplated is depicted in greater detail in FIG. 6. As shown there, the cassette includes a rigid MEMS holder or support 130, a plurality of MEMS sensors or other MEMS devices 132, front cover 134 and membrane backing 136. The holder or support 130 is preferably made of rigid plastic or other suitable material. A plurality of passageways 138 for fluid flow are provided in the MEMS holder, for communicating the desired fluid to the desired MEMS sensor or other device. As illustrated in FIG. 6, three such fluid passageways 138 are shown for initial condition, in-process, and finished product characteristic sensing. The passageways are preformed into the MEMS holder, and communicate with three arrays of MEMS device-receiving areas 140, which are adapted to receive the desired MEMS sensors or other devices. The center fluid passageway communicates with two rows of MEMS device receiving areas that flank the passageway. The other two passageways communicate with a single row of MEMS devices. The size of the array and number of MEMS sensors or other devices may be varied as needed for a given treatment procedure to provide the desired sensing capability. For those MEMS sensors or other devices that require an electrical power source, the rigid holder may include a plurality of electrical contacts 142. Embedded or embossed electrical leads in the holder may extend between the contacts and the appropriate areas 140 for mounting MEMS sensors or other devices that require a voltage source.

The MEMS holder and MEMS sensors/devices are contained beneath the clear cover plate 134, which is sealed to the holder 130, as by adhesive, sonic or solvent bonding, to form the passageways 138. The clear cover allows for the transmission of light to or from associated optical light sources or receivers in the MEMS cassette reader. The flexible membrane 196 attached to the underside of the MEMS holder allows for actuation of valves, pumps or other devices associated with the MEMS cassette, as described in more detail later.

Turning to FIG. 7A, which is a plan view of the MEMS cassette or carrier 98, the initial condition analysis sample line 144 communicates with a first fluid passageway 138a in the MEMS cassette that communicates with a plurality of MEMS sensors for sensing viral or pathogen markers (e.g., a DNA analysis that may reveal the presence of an unwanted virus or bacteria), blood type, lipid level, platelet count and red cell count. The inlet to each MEMS sensors may be controlled by a valve 141, which may be macro-scale valve that controls flow of the initial fluid to the MEMS sensor or by MEMS-scale valves, which are available from a variety of sources using various principles, such as surface tension, flexing membranes or the like. It is contemplated that the initial condition line would communicate, in an apheresis procedure, with the whole blood inlet line. Additionally, although the passageways 138 are shown as having closed ends, the passageways may also continue through the cassette and return to the fluid circuit so that, for example, the sample lines are receiving a constant throughput of the fluid to be analyzed.

The next inlet line is the in-process analysis sample line 146, which communicates with the fluid flow passageway 138b in the MEMS cassette for sampling various characteristics of the fluid while the apheresis process is carried out. For example, the in-process fluid may flow through the center passageway 138b to platelet density MEMS sensors, red cell MEMS sensors and MEMS sensors for counting the number of white cells. The in-process flow line may be attached to the platelet-rich plasma line, the packed red cell line or, if desired, with the processing chamber itself.

The final product analysis sample line 148 communicates with the third passageway 138c in the MEMS cassette for determining final product characteristics, such as partial pressure of $CO_2$, the pH, the platelet density, hematocrit or white cell count. It is anticipated that this final product sample line would be connected to the flow line communicating with the final product collection container, although other connection sites, such as the processing chamber itself, are within the scope of this invention.

Although the characteristics described above are these that may be determined in the platelet collection procedure, the user may select or the manufacturer may employ different MEMS sensors with different objectives or for sensing different characteristics, as desired.

Figure 8:
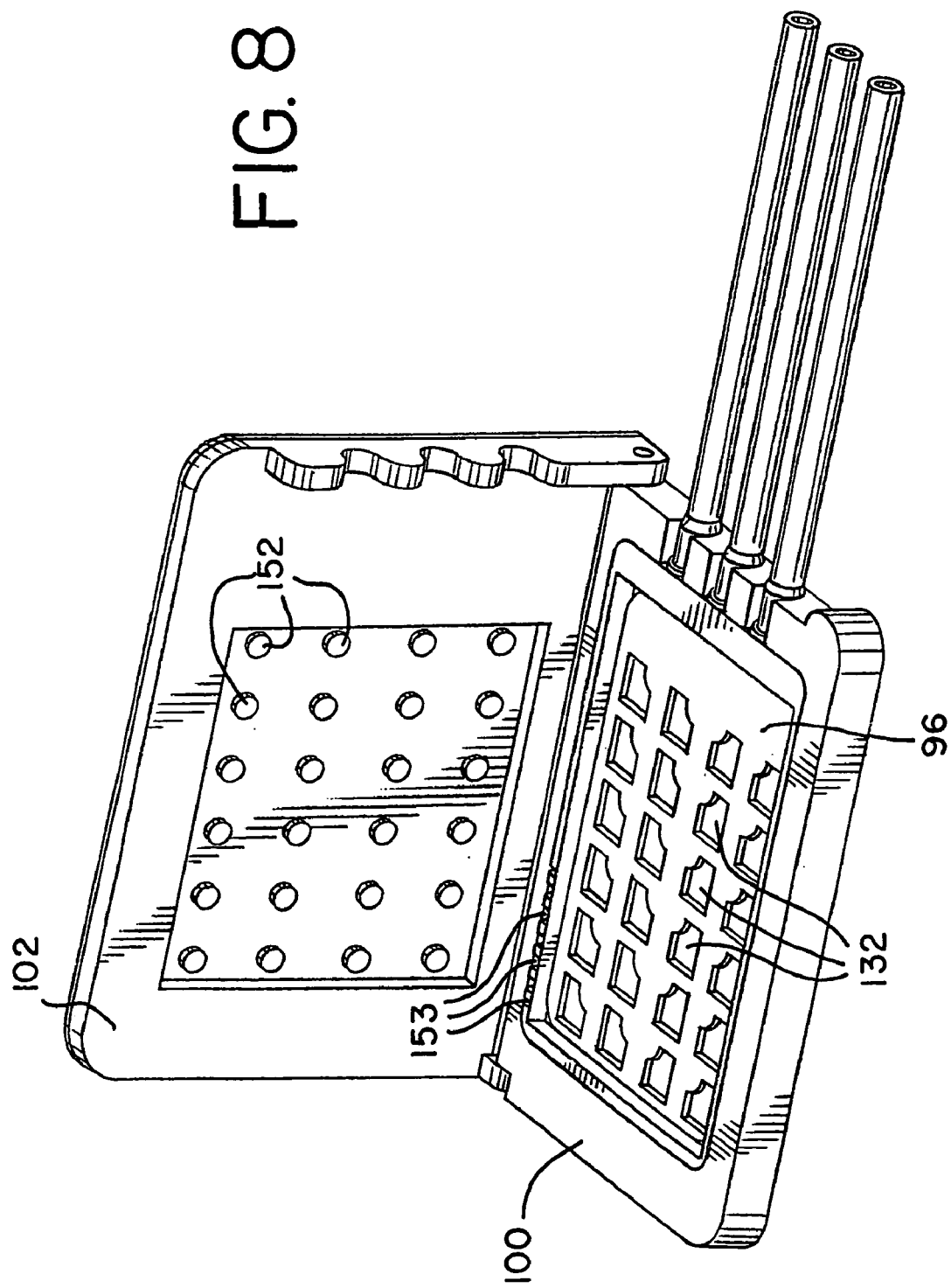
FIG. 8 is a perspective view of the reader/controller for the MEMS cassette.

As shown in FIG. 8, in use, the MEMS cassette or carrier 96 is preferably mounted within a recessed area in the base 100 of the MEMS cassette reader/controller 98. For MEMS devices employing optical read-out, the base preferably includes an array of light emitting fibers or diodes 150 in registration with the appropriate MEMS devices, and the door 102 may include an array of light collectors or receivers 152 in registration with the MEMS devices for the purpose of reading the optical transmission, reflection or refraction by the particular MEMS sensor. The base and/or door also include electrical contacts 153 for connecting with electrical contacts 142 of the cassette for MEMS needing an electrical voltage source. Therefore, it is apparent that the present invention is not limited to a particular type of MEMS sensor or device or to MEMS sensors or devices operating on a particular principle.

Figure 13:
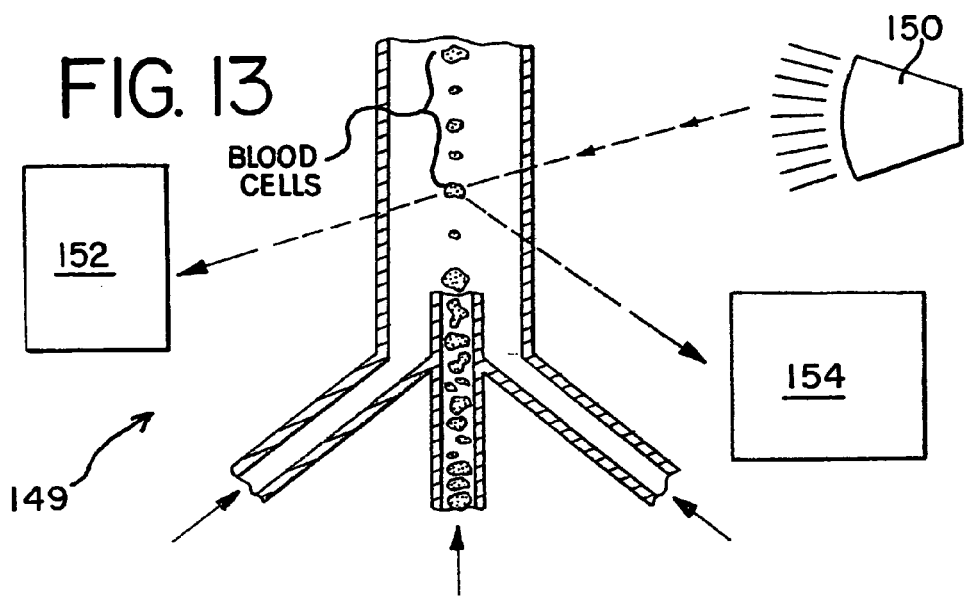
FIG. 13 is a schematic view of MEMS microcytometer that may be used in the present invention.

One example of a MEMS sensor for use in the present invention is illustrated in FIG. 13. The MEMS sensor shown there is a MEMS microcytometer 149, and is believed to have particular promise for cell-related applications. As may be seen there, the microcytometer includes a light source 150 for emitting light, such as coherent laser light, at a single file stream of components, such as cells which may be received from the initial condition, in process or final condition flow lines. Light receivers 152 and 154, receive reflected and refracted light from the particles which, in turn, is used to count or characterize the cells flowing through the line, such as by cell type, cell density or number of cells. Fluorescence detection and light scattering can be used to count and characterize the cells. Such detection may also be combined with immunossays techniques to detect and characterize antibody coated beads and antibody-antigen complexes. This type of MEMS sensor has been previously described by, and may be available from Micronics, Inc., of Redmond, Wash.

Figure 14:
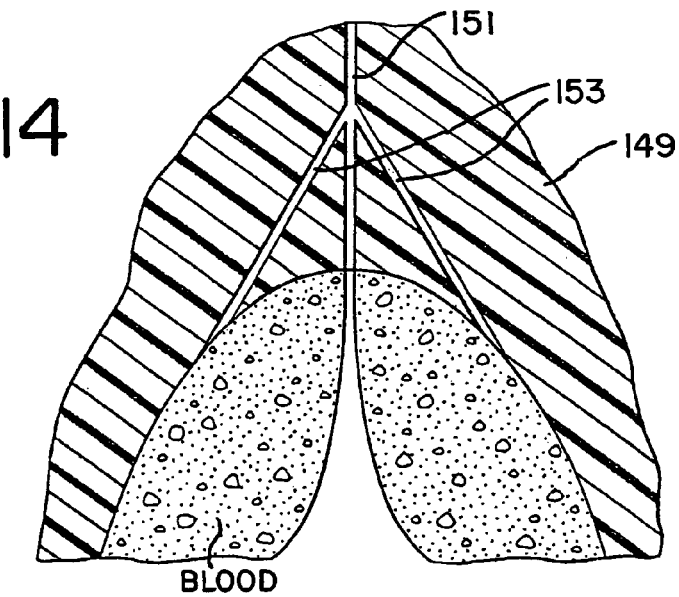
FIG. 14 is a view of the microcytometer of FIG. 13, illustrating the focusing of blood cells using sheath flow.

As shown in FIG. 14, the microcytometer 149 employs a micro-fluidic channel 151 in which fluid flowing in a sheath flow arrangement resulting from liquid flow from the intersecting flow channels 153 forms the cells into single file for analysis. Accordingly, it is within the concept of the present invention that the MEMS cassette may also include additional fluid channels 153, as appropriate, for receiving liquids or gases (such as saline, water, reagents, or other liquids or gases) that may be used in connection with the MEMS sensors.

Figure 17A:
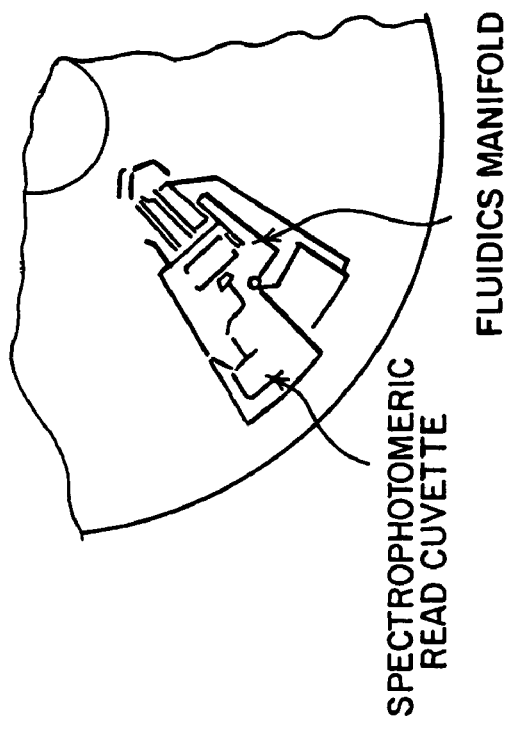
FIG. 17a is a plan view of a compact disc employing a microfluidic manifold and a spectrophotometric cuvette.
Figure 17B:
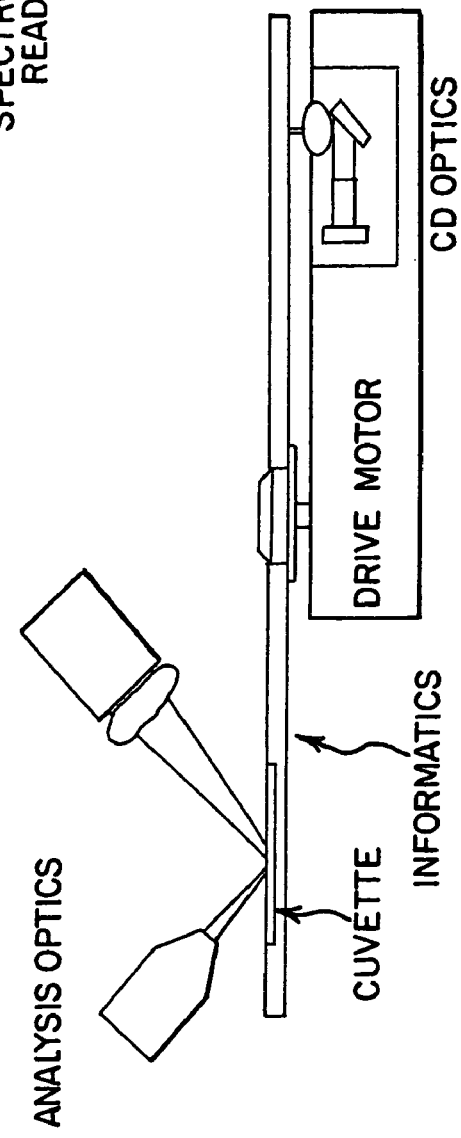

Another MEMS device that may be suitable for application in the present invention is a MEMS sensor based on centrifugal microfluidics analysis. One or more small rotating compact discs may be mounted in the MEMS cassette, which disc may be read by an optical disc reader. The disc employs, for example, a micro-fluidics manifold and spectrophotometric cuvette formed on the surface of the disc. FIG. 17 diagrammatically depicts such a device, which has been proposed by and may be available from Gamera Bioscience of Medford, Mass.

Microfluidic mixing devices, capillary connectors employing microchannels, and membrane micro-valves available from TMP of Enscheda, Netherlands, and thin-walled compliant plastic structures, micro-fluidic circuits, silicone button pneumatic actuators and micro-valves as disclosed by Lawrence Livermore National Laboratory at the Jul. 15–16, 1999 Knowledge Foundation conference on Novel Microfabrication Options for Biomems, in San Francisco, Calif., are but a few of other MEMS devices that may be incorporated into the MEMS cassette of the present invention.

As noted earlier, the MEMS cassette may include macro-scale valves, for example, as used in the Baxter Amicus® separator for controlling flow through the fluid circuit module sets. These valves and their operation is described in more detail in previously cited U.S. Pat. No. 5,462,416. However, the MEMS cassette may also employ MEMS-scale valves 141, as illustrated in FIG. 7a.

Figure 15A:
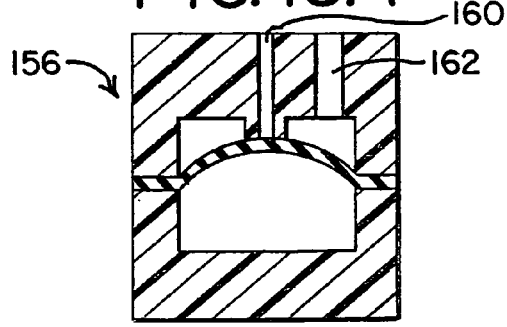
FIGS. 15a and 15b are cross-section views of a bistable valve that may be used in the MEMS cassette of the present invention.
Figure 15B:
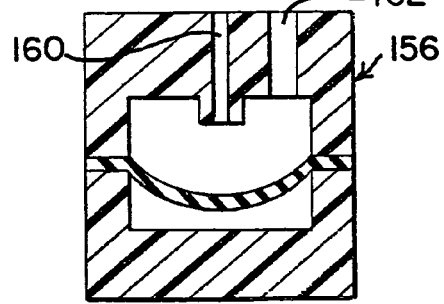

A wide variety of MEMS-scale valves are available. For example, FIGS. 15a and 15b show a bi-stable valve 156 employing a membrane 158 that flexes between a closed position, blocking inlet passageway 160 as shown in FIG. 15a and an open position as shown in FIG. 15b allowing flow between the inlet passageway and outlet passageway 162. The valve presumably opens when the pressure in the valve chamber exceeds a threshold amount, at which time the membrane moves from the stable closed position to the stable open position. The valve moves to the stable closed position when the pressure in the valve chamber drops below a certain threshold value, causing the membrane to move from the stable open position to the stable closed position. Such a bistable microvalve was described by the Institute for Mikrostukturtechnik, at the July, 1999 "Novel Microfabrication Options for Biomems, Technologies & Commercialization Strategies" conference sponsored by the Knowledge Foundation. This is but one example of a MEMS scale valve that may be used in the MEMS cassette. It is also known to use micro-channels and surface tension to form MEMS scale valves, with the valve opening when fluid pressure exceeds a certain threshold to overcome the effects of surface tension. Such valves may also find use in a MEMS cassettes of the type disclosed here.

Figure 9:
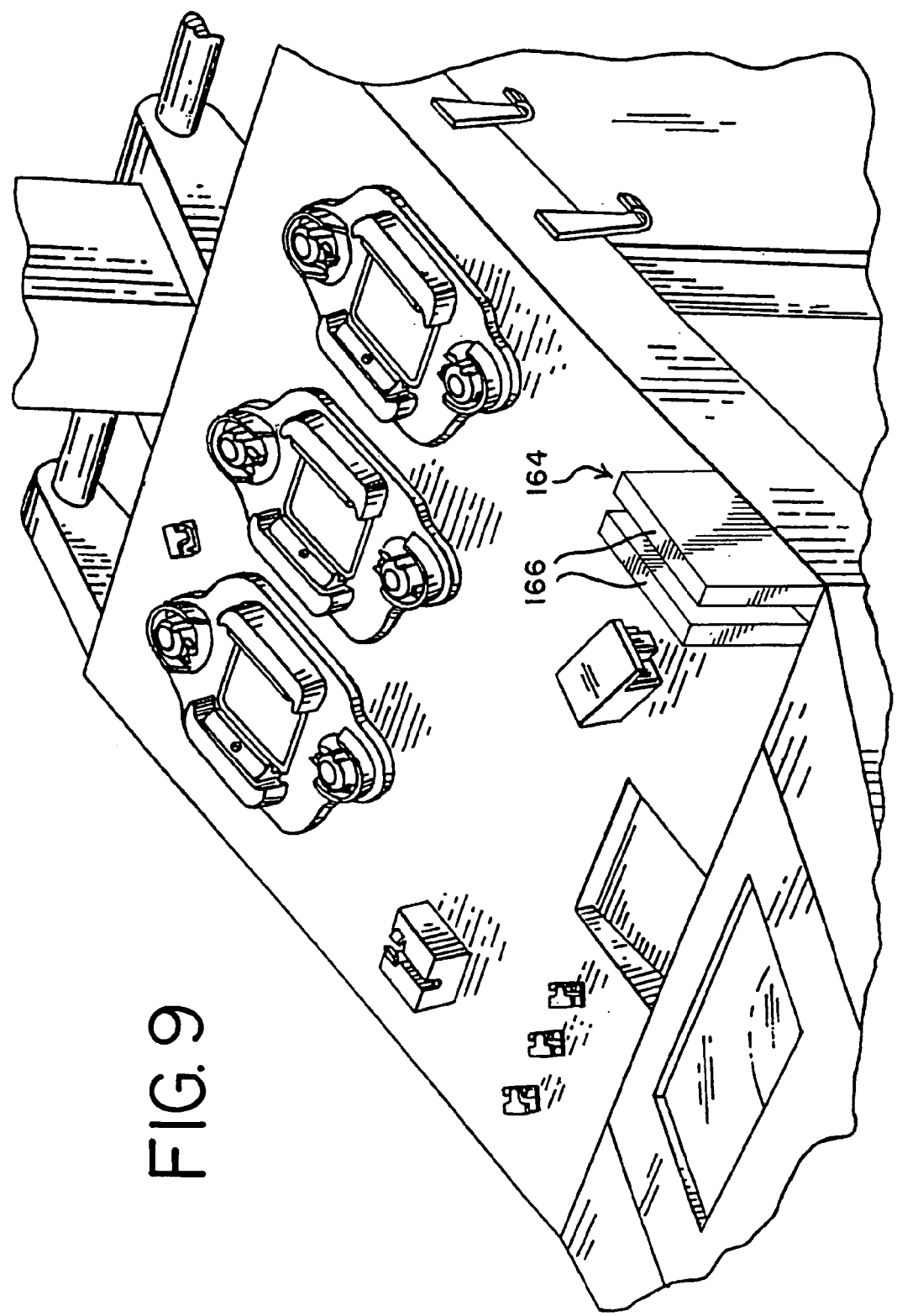
FIG. 9 is an enlarged perspective view of the device of FIG. 3, embodying an alternative MEMS cassette reader/controller.
Figure 10:
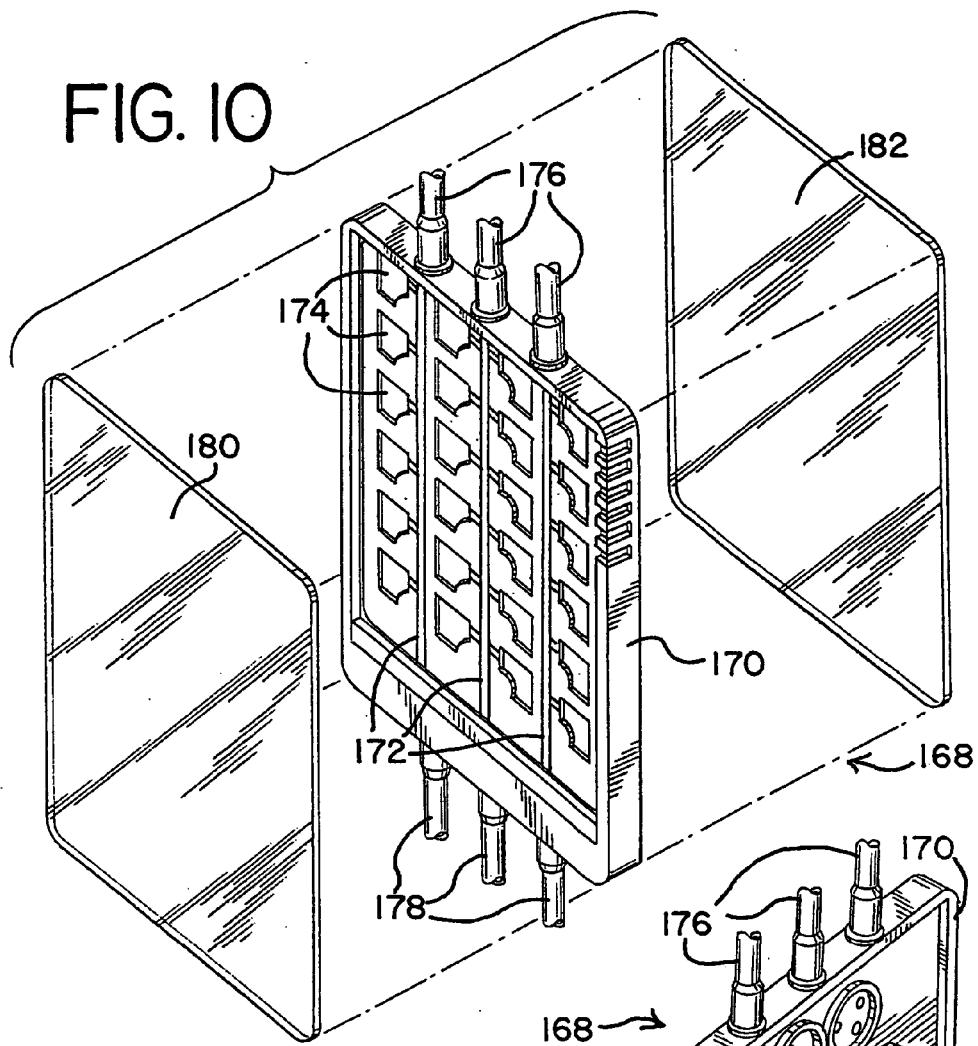
FIG. 10 is an exploded perspective view of a MEMS cassette that may be used with the reader/controller shown in FIG. 9.
Figure 11:
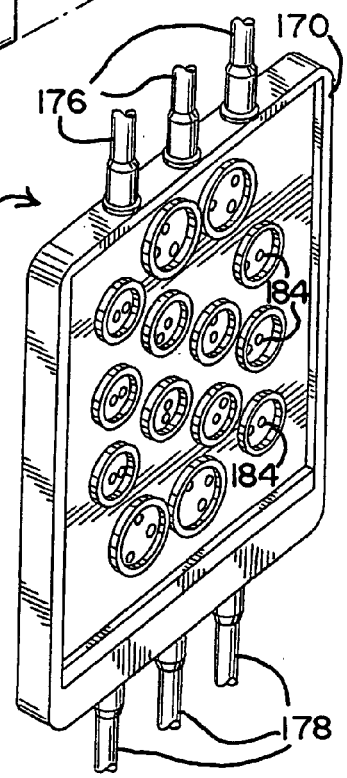
FIG. 11 is a rear perspective view of the assembled MEMS cassette of FIG. 10, illustrating macro-scale valve modules for fluid flow control.

An alternative design for the MEMS carrier or cassette and the cassette reader/controller is shown in FIGS. 9–11. As shown in FIG. 9, a cassette reader/controller 164 comprises a pair of upstanding walls 166 defining a MEMS cassette-receiving slot between them. One wall has a function similar to the base 100 of the prior embodiment and the other wall functions in a manner similar to the door of the prior embodiment. In other words, one wall includes an array of light emitting fibers, diodes or the like, and any appropriate electrical contacts for cooperation with the MEMS devices in the MEMS cassette. The facing wall includes an array of light receivers for cooperating with the MEMS sensors and for reading the characteristics sensed. As before, one of these upstanding walls may also include macro-scale valves for actuating or controlling flow through the MEMS cassette, or the MEMS cassette may include MEMS-scale valves for controlling fluid.

FIG. 10–11 depicts an alternative MEMS cassette 168 for use with reader/controller 164. The MEMS cassette 168 includes a base 170 having preformed fluid passageways 172 and pre-formed MEMS receiving or mounting areas 174 that may be connected to the passageways as desired for allowing fluid flow from the passageway to the MEMS sensor. As may be seen in FIG. 10, the three fluid pathways extend fully through the base from inlets 176 to outlets 178. A clear 180 cover is mounted on one side of the base and a flexible membrane 182 on the other side of the base.

As shown in an underside view, in FIG. 11, valve module areas 184 are provided in the cassette which may be opened or closed by macro-scale valve members which depress the flexible membrane to contact and close against a valve module to block flow between the passageway and MEMS device or, upon release, to open a particular valve module to fluid flow. The valve opening and closing arrangement is preferably comparable to that already employed in the Baxter Amicus® centrifuge, which is described in detail in the U.S. Pat. No. 5,462,416.

Figure 12:
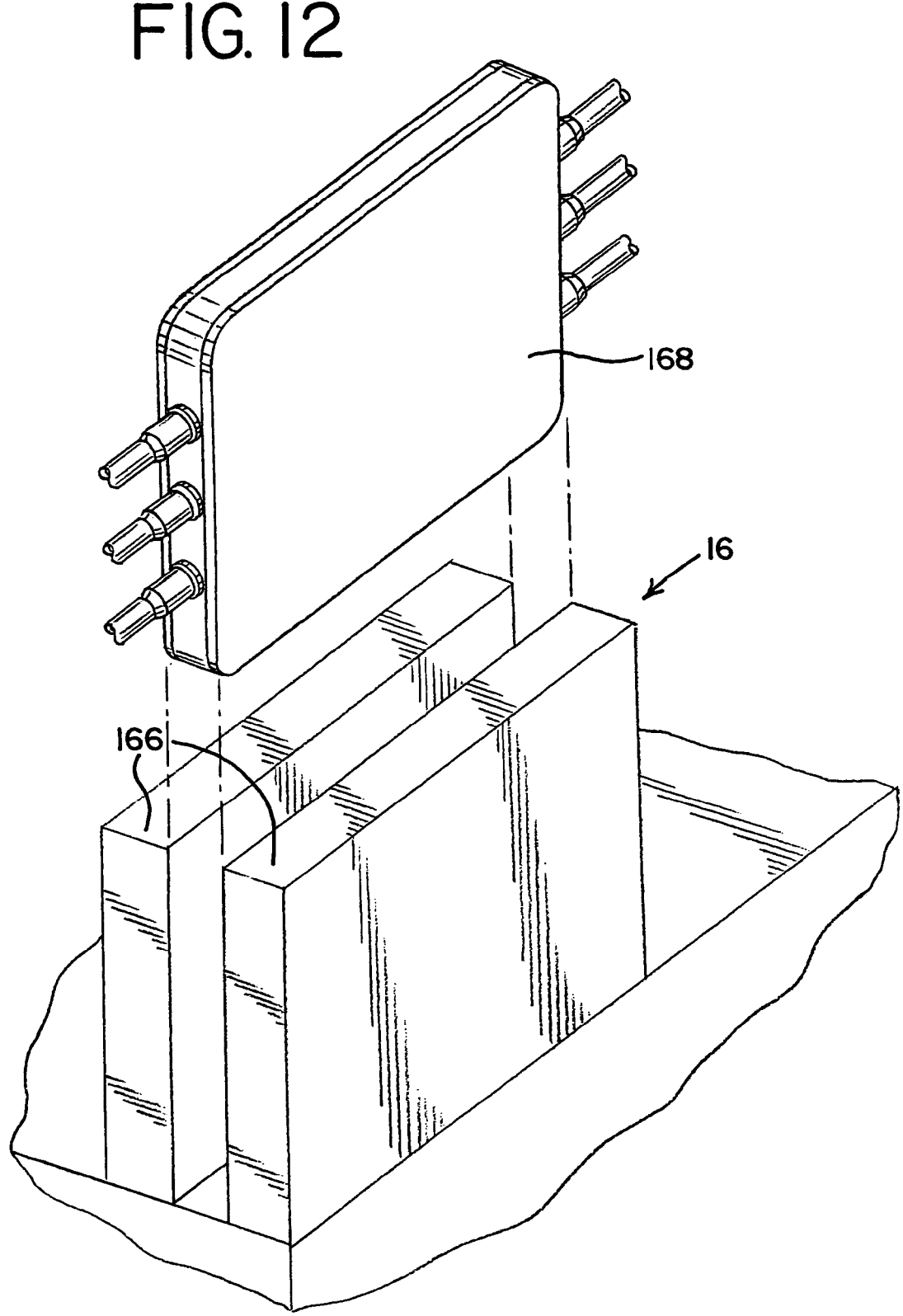
FIG. 12 is an enlarged perspective view showing the interfit between the MEMS cassette of FIG. 10 and the reader/controller of FIG. 9.

As illustrated in FIG. 12, this alternative embodiment of the MEMS reader 164 and cassette 168 permits very easy loading of the cassette during installation of the disposable by sliding the cassette downwardly between the upstanding walls 166 of the MEMS cassette reader/controller.

Figure 16:
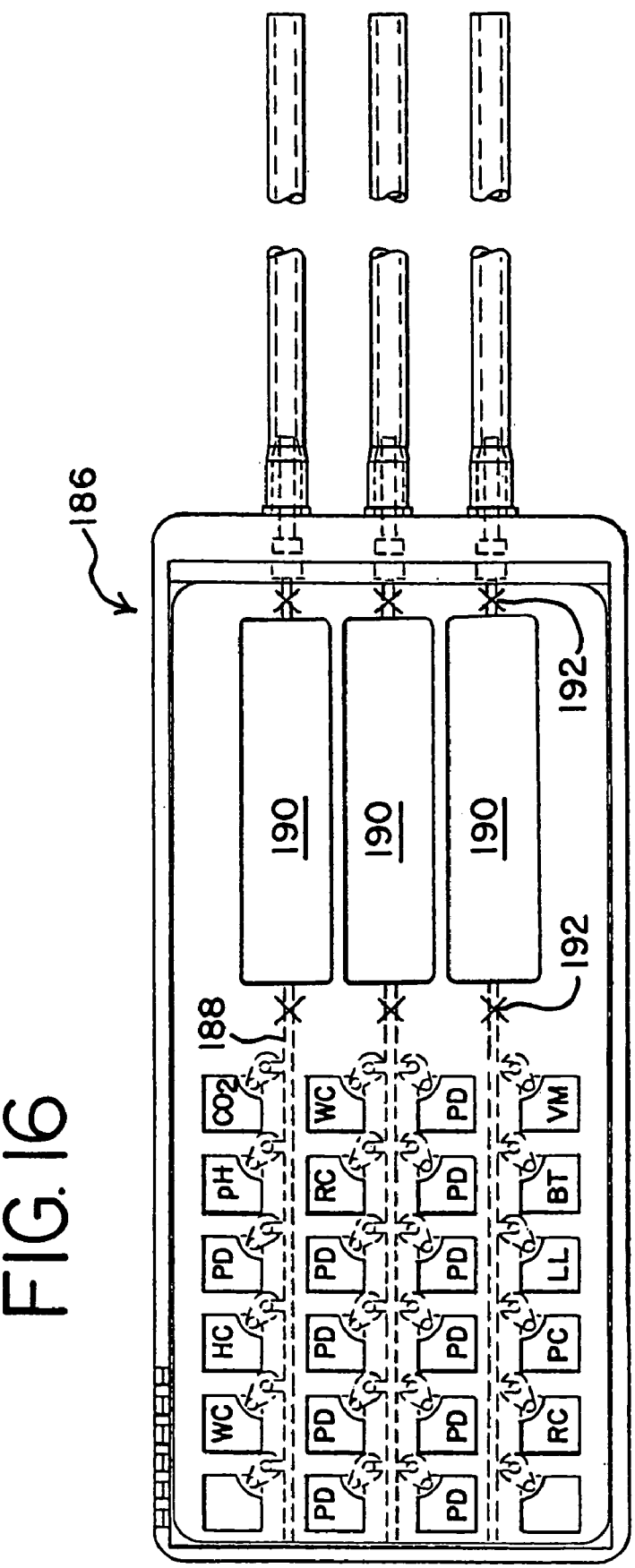
FIG. 16 is a top plan view of an alternative MEMS cassette embodying the present invention, which includes fluid pumping chambers for pumping fluid through the cassette.

FIG. 16 illustrates another embodiment of a MEMS cassette or carrier 186 in accordance with the present invention. The earlier described cassettes rely on pressure within the tubing set (created by peristaltic pumps 92) for moving the selected fluid into and through the MEMS cassette. However, the MEMS cassette may itself have pumping chambers for moving fluid through the cassette and, indeed, through the tubing set, if desired. FIG. 16 shows such a MEMS cassette 186.

As illustrated in FIG. 16, MEMS cassette 186, comparable to previously described embodiments, includes three internal passageways 188 communicating with inlet flow tubing for sensing initial condition, in-process and final condition characteristics. In the FIG. 16 embodiment, however, each passageway also communicates with a respective pumping chamber 190. The pumping chamber preferably has one wall defined a flexible membrane bonded to one side of the cassette. Flexing of the membrane by mechanical or pneumatic pressure alternatively reduces and increases the size of the chamber, resulting in a pumping action. Inlet and outlet valves 192 at each end of the pumping chamber, which are alternatively opened and closed, control the direction of flow through the pump. As pointed out earlier, this pumping may be used only to move the desired fluid through the MEMS cassette or may also be used to move fluid through the entire disposable fluid circuit, if desired.

Figure 18A:
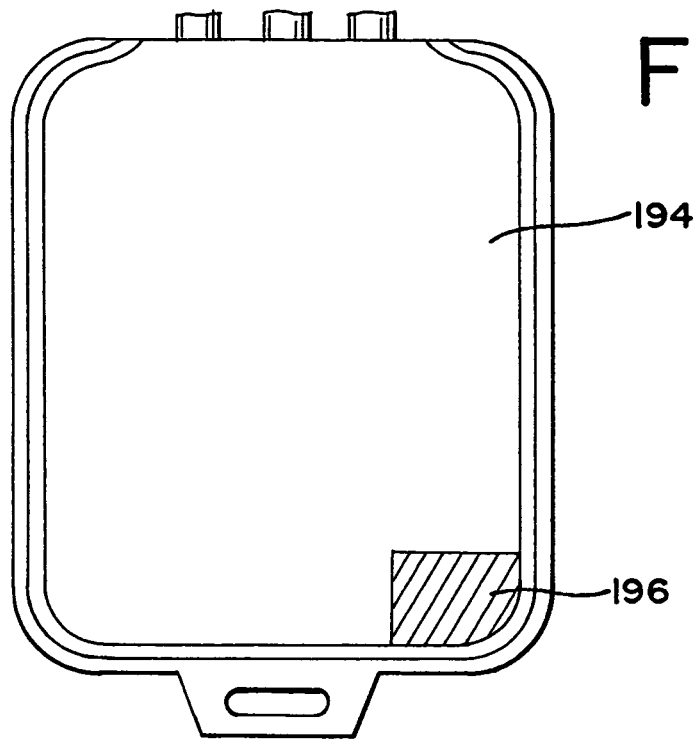
FIG. 18a is a plan view of a blood component storage container having a MEMS sensor mounted in or carried on the container wall for accessing the contents.
Figure 18B:
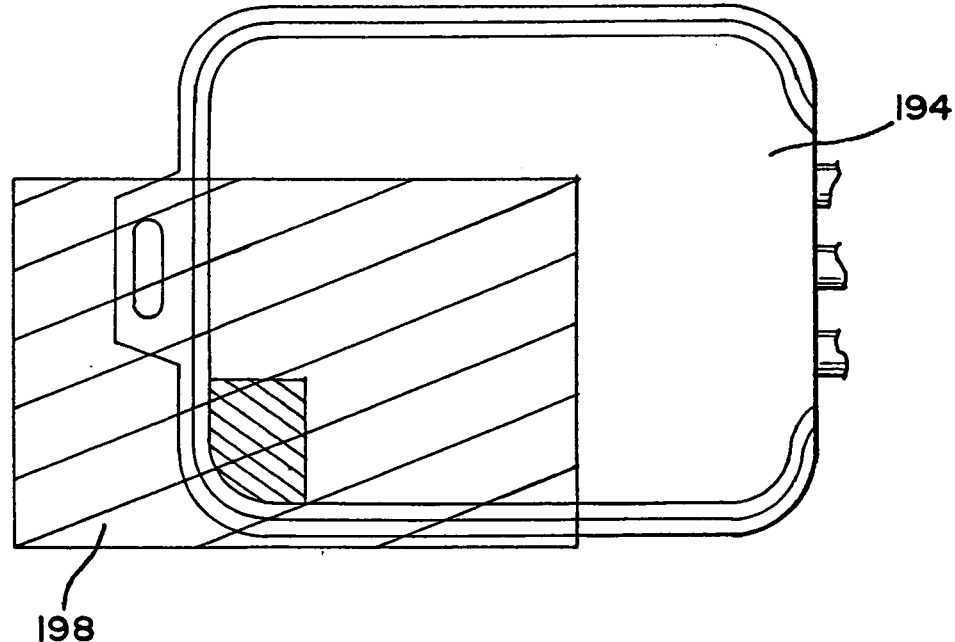
FIG. 18b is a plan view of the container of FIG. 18a with a reader for reading the MEMS sensor.

FIG. 18a shows a blood component container 194 with a MEMS sensor 196 carried by or embedded in the wall of the container for sensing a selected characteristic of the blood component in the container. The MEMS sensor may be adapted to access the container contents through a frangible part of the container wall or through a piercing member associated with the sensor, and may be adapted to test for bacterial contamination and/or pH of the stored blood component. This would have particular application in sensing the blood component just before administration to a patient to assure that the pH and bacteria levels are acceptable.

After a suitable assay period required by the MEMS sensor, the results may be read directly from the MEMS sensor. Alternatively, the MEMS sensor may be read by a reader 198 such as an automated optical, magnetic or electronic device, suitable for the particular MEMS sensor mounted on the bag.

Although described in terms of one or more specific embodiments, the present invention is not limited to the specific structures disclosed for illustrative purposes, and includes such changes or modifications as may be apparent to one skilled in the field upon reading this description.

The invention claimed is:

1. A biological suspension processing system comprising:
    a blood treatment device for treating one or more components of a biological suspension;
    a human subject;
    a first fluid flow path, wherein said first fluid flow path is in continuing, direct communication with the vascular system of the human subject and the treatment device for introducing blood from the human subject into the treatment device;
    a second fluid flow path communicating with the treatment device for withdrawing a constituent of the blood from the treatment device;
    at least one microelectromechanical sensor communicating with one of said fluid flow paths for sensing either a biological or a chemical characteristic of the fluid within the flow path while said first fluid flow path is in continuing, direct communication with the vascular system of the human subject; and
    a controller adapted to receive signals from said sensor and control the blood treatment device in response thereto.

2. The system of claim 1 in which the sensor generates a signal responsive to one or more selected characteristics of the fluid in one of the fluid flow paths.

3. The system of claim 1 in which the second fluid flow path communicates with the human subject, the treatment device is adapted to add anticoagulant to the blood in the first fluid flow path, the selected characteristic includes the hematocrit of blood in the first fluid flow path, and the controller controls the addition of anticoagulant into the first fluid flow path.

4. The system of claim 1 in which the controller controls the treatment device in response to the signal to avoid one or more deleterious consequences to the human subject.

5. The system of claim 1 in which the controller controls the treatment device in response to the signal to withdraw a constituent of desired quality.

6. The system of claim 1 in which the controller controls the treatment device in response to the signal to withdraw a constituent of a desired quantity.

7. The system of claim 1 in which the controller controls the treatment device in response to the signal to withdraw a constituent that is depleted of an undesired component.

8. The system of claim 7 in which the undesired component is white cells.

9. The system of claim 1 in which the controller controls the treatment device in response to the signal to withdraw a desired constituent.

10. The system of claim 9 in which the desired constituent is platelets.

11. The system of claim 9 in which the desired constituent is red cells or plasma.

12. The system of claim 1 in which the sensor senses platelets and the controller controls the treatment device to withdraw a selected minimum quantity of platelets.

13. The system of claim 1 further comprising a fluid management module carried by the first fluid flow path between the vascular system of the human subject and the treatment device, said fluid management module adapted to receive blood from the vascular system of the human subject via the first fluid flow path and control the amount of blood introduced into the treatment device.

14. The system of claim 1 further comprising a container communicating with the second fluid flow path for receiving the withdrawn constituent, the system being adapted to provide tracking information for associating with the container the particular characteristic sensed by at least one sensor.

15. The system of claim 14 in which the system further comprises machine readable or human readable data storage media carried by the container, the data storage media storing information regarding the particular characteristic sensed by at least one sensor.

16. The system of claim 15 in which the data storage media comprises a bar code label on the container.

17. The system of claim 15 in which the data storage media comprises an electronic data storage device.

18. The system of claim 15 in which the electronic data storage device has a non-volatile semiconductor memory.

19. The system of claim 15 in which the data storage media comprises at least one icon carried by the container and representative of the sensed characteristic.

20. The system of claim 15 in which the suspension includes one or more blood components and the blood component withdrawn is a cellular component, and the container is for storing the cellular component withdrawn, and the data storage media includes data regarding the type, quality, purity, quantity or concentration of the cellular blood component in the container.

* * * * *